US011371032B2

(12) United States Patent
Marjamaa et al.

(10) Patent No.: US 11,371,032 B2
(45) Date of Patent: Jun. 28, 2022

(54) BETA GLUCOSIDASE WITH HIGH GLUCOSE TOLERANCE, HIGH THERMAL STABILITY AND BROAD PH ACTIVITY SPECTRUM

(71) Applicant: Teknologian tutkimuskeskus VTT Oy, Espoo (FI)

(72) Inventors: Kaisa Marjamaa, Vtt (FI); Anu Koivula, Vtt (FI); Nina Aro, Vtt (FI); Tiina Pakula, Vtt (FI)

(73) Assignee: Teknologian Tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 16/972,016

(22) PCT Filed: Jun. 4, 2019

(86) PCT No.: PCT/FI2019/050423
§ 371 (c)(1),
(2) Date: Dec. 4, 2020

(87) PCT Pub. No.: WO2019/234294
PCT Pub. Date: Dec. 12, 2019

(65) Prior Publication Data
US 2021/0284983 A1 Sep. 16, 2021

(30) Foreign Application Priority Data
Jun. 5, 2018 (FI) .................................... 20185511

(51) Int. Cl.
*C12N 9/42* (2006.01)
*C12P 19/14* (2006.01)
(52) U.S. Cl.
CPC ............ *C12N 9/2445* (2013.01); *C12P 19/14* (2013.01); *C12Y 302/01021* (2013.01)
(58) Field of Classification Search
CPC .................. C12N 9/2445; C12P 19/14; C12Y 302/01021
See application file for complete search history.

(56) References Cited

U.S. PATENT DOCUMENTS 5,747,320 A * 5/1998 Saha .............. C12Y 302/01021
435/161
2021/0284983 A1* 9/2021 Marjamaa ............ C12N 9/2445

FOREIGN PATENT DOCUMENTS

| CN | 101955922 A | 1/2011 |
| CN | 104988125 A | 10/2015 |
| CN | 107828806 A | 3/2018 |
| EP | 2824178 A1 | 1/2015 |
| EP | 2824178 A1 | 9/2018 |
| WO | 2013181760 A1 | 12/2013 |
| WO | 2014059541 A1 | 4/2014 |
| WO | 2014166326 A1 | 10/2016 |
| WO | 2014059541 A1 | 9/2018 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Gustafsson et al., Codon bias and heterologous protein expression. Trends in Biotechnology, Jul. 2004, vol. 22(7): 346-353. (Year: 2004).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Colabardini, Ana C et al.,"Expression of Two Novel [beta]-Glucosidases from Chaetomium atrobrunneumin Trichoderma reesei and Characterization of the Heterologous Protein Products", Molecular Biotechnology, Humana Press, Boston, vol. 58, No. 12, Oct. 2016 (Oct. 6, 2016), pp. 821-831.
Cao, Huifang et al: "A highly glucose-tolerant GH1 [beta]-glucosidase with greater conversion rate of soybean isoflavones in monogastric animals", Journal of Industrial Microbiology and Biotechnology, Basingstoke, GB, vol. 45, No. 6, May 9, 2018 (May 9, 2018), pp. 369-378.
Yang, Fang et al.:"Overexpression and characterization of a glucose-tolerant [beta]-glucosidase from T. aetearoense with high specific activity for cellobiose", Applied Microbiology and Biotechnology, Springer, DE, vol. 99, No. 21, May 9, 2015 (May 9, 2015), pp. 8903-8915.
Ramani, Gurusamy et al: "Molecular cloning and expression of thermostable glucose-tolerant [beta]-glucosidase of Penicillium funiculosum NCL1 In Pichia pastorisand its characteriza", Journal of Industrial Microbiology and Biotechnology, Basingstoke, GB, vol. 42, No. 4, Jan. 28, 2015 (Jul. 28, 2015), pp. 553-565.
Altschul, Stephen F. et al.: "Basic Local Alignment Search Tool", J. Mol. Biol. (1990) 215, pp. 403-410.
Nordahl Petersen, Thomas et al.: "SignalP 4.0: discriminating signal peptides from transmembrane regions", Nature methods, vol. 8, No. 10, Oct. 2011, 3 pages.
Penttilä, Merja et al.: "A versatile transformation system for the cellulolytic filamentous fungus Trichoderma reesei", Gene, 61 (1987), Elsevier, pp. 155-164.

(Continued)

*Primary Examiner* — Ganapathirama Raghu
(74) *Attorney, Agent, or Firm* — Merchant & Gould P.C.

(57) ABSTRACT

The present invention discloses a polypeptide having beta-glucosidase activity. The activity is retained also in high glucose concentration. The invention also discloses an isolated polynucleotide, a nucleic acid construct and a recombinant host usable in production of said polypeptide, and a method for producing the polypeptide. Further the invention discloses compositions including the polypeptide and method of using the polypeptide in hydrolysis or synthesis.

8 Claims, 7 Drawing Sheets
Specification includes a Sequence Listing.

(56) References Cited

OTHER PUBLICATIONS

Sipos, Balint et al.: "Characterisation of Specific Activities and Hydrolytic Properties of Cell-Wall-Degrading Enzymes Produced by Trichoderma reesei Rut C30 on Different Carbon Sources", Appl. Bochem Biotechnol (2010) 161: pp. 347-364, Humana Press 2009.
I-Son. Ng et al.: "Dynamic synergistic effect on Trichoderma reesei cellulases by novel beta-glucosidases from Taiwanese fungi", Bioresource Technology 102 (2011), pp. 6073-6081.
Smith T. F. et al.: "Identification of Common Molecular Subsequences", J. Mol. Biol. (1981) 147, pp. 195-197.

* cited by examiner

```
SEQ ID NO: 2    QEYVTTTCYSRRFQCTQSNVTRYHPQFFSTILNDTVRYATSVPSPITIRKYAAPYTIN
SEQ ID NO: 3    QGYVTTTCYIDRFQCTQLASSRQYHFQPFENALESTVRYATSVPSPITIRTYAFPYSEA
SEQ ID NO: 1    QQINITTTGYTERFECTPSFPTRNYLRPPSYTLNETVRYAISVQAPTTIRTYQPAYTDA
                 *  ******  * **  * *    *     ** ****** **  ****** *  *

SEQ ID NO: 2    VKELTTSNSISTNGSNVPDQTSISATSTKDPYQQAANSESNLQADLENYTTTGLPSTTVS
SEQ ID NO: 3    VKELTTSPATTTKQSNLPQQTLITETDTHDPNSQAANSSLNQSVELENYTTTGLYNTTVT
SEQ ID NO: 1    VTRLTTTLSTSTNGSNLPNQTVITATEATDPYSQAANSELNLQADIRNYTTTGLYSTTVS
                * ***  **  **  *   *   *    ** ***** *     ********  ***

SEQ ID NO: 2    PTFVPSSELVLPPRDYFGPTSCYKFQDFVTGVAGSAAQISGAIGLDGRSFSLLSRLVSD
SEQ ID NO: 3    PTPVPSTDLVLPPRDYFGPTDCYNFPDDFISGVAGSAAQVSGANALSCRSPTILSKLVNS
SEQ ID NO: 1    PTRIPSRELVLPPRDYFGPTDCYEFPEDFVFGVRGSAAQESGAIGIESRTPYLSSNFIQS
                **  **  *********** **  *  **  ** *****  **   *  *

SEQ ID NO: 2    DKPRDYVINENYFLYKQSIQRLAAMGVEYYSFTIPNTRILSFALPGTSVWQSGIDSYSDL
SEQ ID NO: 3    SQPRDYVINSNYYLYKQDIQRLAAMGVKYYSFSIPNTRILSFVLPGSPVWQDGIRSYSDL
SEQ ID NO: 1    SSPRDYVINSNYFLYKQDIQRLAALGVKYYSFSIPNTRILSFVLAGTSVWQGGIDSYSDL
                 **********  *****  ****  * **** **********  *  ***  * ****

SEQ ID NO: 2    IDTVLDAGSWIPVVTMLHFESFLMFVASD-NITRHPDIGYSNGGYQSETFVDAFVNYGKVL
SEQ ID NO: 3    IRTVLDAGNWPIATLIEFDTPNVFVSSDENSTARFDIGYNBGGYQNETFVDAYVNYAKIV
SEQ ID NO: 1    IETVLDSNWILPVVTMLHFSTPNIFLASD-NITAHPDIGYNRGGYQSETFVNAFVNYGKVL
                * ****    *   *  *   *  * *  *  *  ****** ****  ****  ***

SEQ ID NO: 2    LSEYADRVPINYTFNSSPLLYAFNFSGADSNVVRASAQVYHFYSDTLSATCRIGIKFNDNFG
SEQ ID NO: 3    LSRFADRVPINITFNESPLLYSFNFAGISNVVSAHAQVYHFYSDELKATQGIGIKFNDNFG
SEQ ID NO: 1    LTRFADRVPINYTFNESPLLYSFNFDGISNVVEAHRSLYHFYSDTLNATQKIGLRLNDNFG
                *  *******   *** ***** ***  * ** **   **** *  **  ***  ******

SEQ ID NO: 2    VPKDPNSSSHVLAADSFQEMQLGIFANPIFLGRQYFPSVLDTSLPGANSLSRSELRSIRNT
SEQ ID NO: 3    VPRNPKNSSDVEAANRFQEMQLGLFANPIFLGQQYPDSILNTLGARPLGRQELSYIAMT
SEQ ID NO: 1    VPRNPSNESSVLAASRFQEMQLGVFTNPIFLGQQYPDSILNTLPGARPLTGEELEYIKNT
                **   *  *    *  **** *** *******  **  **   **        *    *

SEQ ID NO: 2    SDFFGIDFYTAFVVSPANSGIEACAANQSSSSELFPYCVRQSTRDNYCWNIGYRSSSYVY
SEQ ID NO: 3    SDFFGIDFYTATVVSQPAGGIIDACRANFSVANSLFPYCVVQSTRDNIYCMNIGYRSQSYVY
SEQ ID NO: 1    ADFFGIDFYTATVVSQPAGGIIDACAFNTSADNSLFPYCVVQSTRNNVYCMNIGYRSQSFVY
                 ***********  **   *  ***         * ******  **  ** ****** *  ****

SEQ ID NO: 2    ITPTHFREYLFYLMNTFRSPILVSSPGPVSAEAESSELSDQLFDSPRSVYLSFMSRIL
SEQ ID NO: 3    ITPTYLREYLNSLRSTRSHPVFVTESGPPVFAEAE-KELSDQQFSDPRSIFYLSFMSRIL
SEQ ID NO: 1    ITPTYLREYLSYLWNTFQRPVIVTEFGPFVTDESLRAELSDQLFDSPRSVYLSYMSRIL
                **** ****   *  *  * * * * **  *    *  ****  * **** **** ****

SEQ ID NO: 2    KSIYSDGVHVMGALANSFVDSNWEFGDYTQQFGIDAVVNRTTQGRYYSRAPFDIVDFVKTRQ
SEQ ID NO: 3    KAIHEDGVHVMGALANSWADSNWEFGDYSQQFGMQVVVNRTTQGRFYKRELFDIVDFVGARS
SEQ ID NO: 1    KAIWEDGVHVMGALANEFMSKWEFGDYSAQFGMQVVVNRTTQGRFYKRAFFDIVDFVCARQ
                *   ***********       *****  *** *  ********* * *  * ****** *

SEQ ID NO: 2    PNKD------
SEQ ID NO: 3    LSSDNGTVS
SEQ ID NO: 1    RQS-------
```

Fig. 5

SEQUENCE LISTING

<160> NUMBER OF SEQ ID NOS: 7

<210> SEQ ID NO 1
<211> LENGTH: 602
<212> TYPE: PRT
<213> ORGANISM: Penicilliopsis clavariiformis

<400> SEQUENCE: 1

```
Gln Gln Ile Tyr Ile Thr Thr Thr Gly Tyr Thr Glu Arg Pro Glu Cys
1               5                   10                  15

Thr Pro Ser Pro Pro Thr Pro His Tyr Tyr Leu His Pro Phe Ser Tyr
            20                  25                  30

Thr Leu Asn Glu Thr Val Arg Tyr Ala Ile Ser Val Gln Ala Pro Thr
        35                  40                  45

Thr Thr Arg Thr Tyr Gly Pro Ala Tyr Thr Asp Ala Val Thr His Leu
    50                  55                  60

Thr Thr Thr Leu Ser Thr Ser Thr Trp Gly Ser Trp Leu Pro Asn Gln
65                  70                  75                  80

Thr Val Ile Thr Ala Thr Asp Ala Thr Asp Pro Tyr Gly Gln Ala Ala
                85                  90                  95

Trp Ser Ser Leu Trp Leu Gln Ala Asp Ile Lys Asn Tyr Thr Thr Thr
            100                 105                 110

Gly Leu Tyr Ser Thr Thr Val Ser Pro Thr Ala Ile Pro Ser Arg Glu
        115                 120                 125

Leu Val Leu Pro Pro Arg Asp Tyr Phe Gly Pro Thr Asp Cys Tyr Glu
    130                 135                 140

Phe Pro Glu Asp Phe Val Phe Gly Val Ala Gly Ser Ala Ala Gln Ile
145                 150                 155                 160

Glu Gly Ala Ile Gly Ile Glu Gly Arg Thr Pro Thr Leu Met Glu Asn
                165                 170                 175

Phe Ile Gln Ser Ser Ser Pro Lys Asp Tyr Val Thr Asn Glu Asn Tyr
            180                 185                 190

Phe Leu Tyr Lys Gln Asp Ile Gln Arg Leu Ala Ala Leu Gly Val Lys
        195                 200                 205

Tyr Tyr Ser Phe Ser Ile Pro Trp Thr Arg Ile Leu Pro Phe Val Leu
    210                 215                 220
```

```
Ala Gly Thr Pro Val Asn Gln Gln Gly Ile Asp His Tyr Asp Asp Leu
225                 230                 235                 240

Ile Glu Thr Val Leu Asp Ser Gly Met Leu Pro Val Val Thr Met Leu
            245                 250                 255

His Phe Asp Thr Pro Trp Ile Phe Leu Ala Ser Asp Asn Ile Thr Ala
        260                 265                 270

His Pro Asp Ile Gly Tyr Asn Asn Gly Gly Tyr Gln Asn Glu Thr Phe
    275                 280                 285

Val Asn Ala Phe Val Asn Tyr Gly Lys Val Leu Leu Thr His Phe Ala
290                 295                 300

Asp Arg Val Pro Ile Trp Val Thr Phe Asn Glu Pro Leu Leu Tyr Ser
305                 310                 315                 320

Phe Asn Phe Asp Gly Ile Asn Asn Val Val His Ala His Ala Glu Leu
            325                 330                 335

Tyr His Phe Tyr His Asp Thr Leu Asn Ala Thr Gly Lys Ile Gly Leu
        340                 345                 350

Lys Leu Asn Asp Asn Phe Gly Val Pro Arg Asn Pro Phe Asn Glu Ser
    355                 360                 365

Asp Val Leu Ala Ala Asn Arg Phe Gln Glu Met Gln Leu Gly Val Phe
370                 375                 380

Thr Asn Pro Ile Phe Leu Gly Gln Gln Tyr Pro Asp Ser Ile Leu Asn
385                 390                 395                 400

Thr Leu Pro Gly Ala Lys Pro Leu Thr Gly Glu Glu Leu Glu Tyr Ile
            405                 410                 415

Lys Asp Thr Ala Asp Phe Phe Gly Ile Asp Pro Tyr Thr Ala Thr Val
        420                 425                 430

Val Ser Gln Pro Ala Gly Gly Ile Asp Ala Cys Ala Lys Asn Thr Ser
    435                 440                 445

Ala Asp Asn Ser Leu Phe Pro Tyr Cys Val Val Gln Glu Thr Lys Asn
450                 455                 460

Val Tyr Gly Trp Asn Ile Gly Tyr Arg Ser Gln Ser Tyr Val Tyr Ile
465                 470                 475                 480

Thr Pro Thr Tyr Leu Arg Glu Tyr Leu Ser Tyr Leu Trp Asn Thr Phe
            485                 490                 495

Gln Lys Pro Val Ile Val Thr Glu Phe Gly Phe Pro Val Phe Asp Glu
        500                 505                 510

Ser Leu Lys Ala Glu Leu Ser Asp Gln Leu Phe Asp Ser Pro Arg Ser
    515                 520                 525

Val Tyr Tyr Leu Ser Tyr Met Ser Glu Ile Leu Lys Ala Ile Trp Glu
530                 535                 540

Asp Gly Val His Val Met Gly Ala Leu Ala Trp Ser Phe Met Asp Asn
545                 550                 555                 560

Trp Glu Phe Gly Asp Tyr Ser Ala Gln Phe Gly Met Gln Val Val Asn
            565                 570                 575

Arg Thr Thr Gln Gln Arg Phe Tyr Lys Lys Ser Phe Phe Asp Leu Val
        580                 585                 590

Asp Phe Val Gly Ala Arg Gln Arg Gly Ser
    595                 600

<210> SEQ ID NO 2
<211> LENGTH: 1809
<212> TYPE: DNA
<213> ORGANISM: Penicilliopsis clavariiformis
```

<400> SEQUENCE: 2

```
cagcagatct acatcaccac caccggctac accgagcgac ccgagtgcac gccctcgcct    60
ccgacgcctc actactatct gcacccttc agctacaccc tcaacgagac tgtccgctac   120
gccatcagcg tgcaggcccc taccaccacg cgcacgtacg gccctgccta caccgacgcc   180
gtcacgcacc tcaccacgac gctcagcacc agcacctggg gcagctggct ccccaaccag   240
accgtcatca ccgccacgga cgctacggac ccctacggcc aggccgcctg gtccagcctc   300
tggctccagg ccgacatcaa gaactacacc accacgggcc tctactcgac cacggtcagc   360
cccaccgcca ttcctagccg cgagctggtc ctgcctcctc gcgactactt cggccccacc   420
gactgctacg agttccccga ggacttcgtc tttggcgtcg ccggcagcgc cgctcagatc   480
gagggcgcca tcggcatcga gggccgcacg cctacgctca tggaaaactt catccagagc   540
agcagcccca aggactacgt gaccaacgag aactacttcc tctacaagca ggacatccag   600
cgcctcgccg ctctcggcgt caagtactac agcttcagca tccctggac gcgcattctc   660
cccttcgtcc tggccggcac gcccgtcaac cagcagggca tcgaccacta cgacgacctc   720
atcgaaaccg tcctcgacag cggcatgctc ccgtcgtca ccatgctcca cttcgatacg   780
ccctggatct tcctcgccag cgacaacatc acggctcacc ccgacatcgg ctacaacaac   840
ggcggctacc agaacgagac tttcgtcaac gccttcgtca actacggcaa ggtcctgctc   900
acccacttcg ccgatcgcgt ccccatctgg gtgaccttca cgagcccct cctctactcc   960
ttcaacttcg acggcatcaa caacgtcgtc cacgctcacg ccgagctgta ccacttctac  1020
cacgacaccc tgaacgccac cggcaagatc ggcctcaagc tcaacgacaa cttcggcgtc  1080
cctcgcaacc ctttcaacga gagcgacgtc ctcgccgcca accgcttcca agagatgcag  1140
ctgggcgtct ttacgaaccc catcttcctg ggccagcagt accccgacag catcctcaac  1200
accctgcctg cgccaagcc tctcaccggc gaggaactcg agtacatcaa ggacaccgcc  1260
gactttttcg gcattgaccc ctacaccgcc accgtcgtca gccagcctgc tggcggcatc  1320
gacgcctgcg ccaagaacac cagcgccgac aactcgctgt cccctactg cgtcgtccaa  1380
gaaacgaaga acgtctacgg ctggaacatt ggctaccgca gccagagcta cgtctacatt  1440
acgcccacct acctccgcga gtacctcagc tacctctgga cacctttca gaagcccgtc  1500
atcgtcaccg agttcggctt ccccgtcttt gacgagagcc tcaaggccga gctgagcgac  1560
cagctgttcg actcgccccg cagcgtctac tacctctcct acatgagcga gatcctgaag  1620
gccatctggg aggacggcgt ccacgtcatg ggcgccctgg cctggtcctt catggacaac  1680
tgggagttcg gcgactacag cgcccagttc ggcatgcagg tcgtcaaccg caccacgcag  1740
cagcgcttct acaagaagtc cttcttcgac ctcgtcgact tcgtcggagc ccgccagcgc  1800
ggcagctga                                                         1809
```

<210> SEQ ID NO 3  
<211> LENGTH: 608  
<212> TYPE: PRT  
<213> ORGANISM: Talaromyces flavus

<400> SEQUENCE: 3

```
Gln Gln Val Tyr Val Thr Thr Thr Gly Tyr Thr Asp Arg Pro Gln Cys
1               5                   10                  15
Thr Gln Leu Ala Ser Ser Pro Gln Tyr His Phe Gln Pro Phe Ser Tyr
            20                  25                  30
```

-continued

Ala Leu Glu Glu Thr Val Arg Tyr Ala Thr Ser Val Pro Ser Pro Thr
             35                  40                  45

Thr Thr Arg Thr Tyr Ala Pro Pro Tyr Ser Ser Ala Val Lys Phe Leu
 50                  55                  60

Thr Thr Ser Pro Ala Thr Thr Thr Trp Gly Asn Trp Leu Pro Gly Gln
 65                  70                  75                  80

Thr Leu Ile Thr Glu Thr Asp Thr His Asp Pro Tyr Gly Gln Ala Ala
             85                  90                  95

Trp Ser Ser Leu Trp Gln Gln Val Glu Leu Glu Asn Tyr Thr Thr Thr
            100                 105                 110

Gly Leu Tyr Trp Thr Thr Val Thr Pro Thr Pro Val Pro Ser Thr Asp
            115                 120                 125

Leu Val Leu Pro Pro Arg Asp Tyr Phe Gly Pro Thr Asp Cys Tyr Asn
130                 135                 140

Phe Pro Asp Asp Phe Ile Phe Gly Val Ala Gly Ser Ala Ala Gln Val
145                 150                 155                 160

Glu Gly Ala Val Ala Leu Glu Gly Arg Ser Pro Thr Ile Leu Glu Lys
                165                 170                 175

Leu Val Asn Ser Ser Gln Pro Lys Asp Tyr Val Thr Asn Glu Asn Tyr
            180                 185                 190

Tyr Leu Tyr Lys Gln Asp Ile Gln Arg Leu Ala Ala Met Gly Val Lys
            195                 200                 205

Tyr Tyr Ser Phe Ser Ile Pro Trp Thr Arg Ile Leu Pro Phe Val Leu
            210                 215                 220

Pro Gly Ser Pro Val Asn Gln Glu Gly Ile Lys His Tyr Asp Asp Leu
225                 230                 235                 240

Ile Asn Thr Val Leu Asp Ala Gly Met Gln Pro Ile Ala Thr Leu Ile
                245                 250                 255

His Phe Asp Thr Pro Trp Val Phe Val Ser Ser Asp Glu Asn Phe Thr
                260                 265                 270

Ala Arg Pro Asp Ile Gly Tyr Asn Asn Gly Gly Tyr Gln Asn Glu Thr
            275                 280                 285

Phe Val Asp Ala Tyr Val Asn Tyr Ala Lys Ile Val Leu Ser His Phe
            290                 295                 300

Ala Asp Arg Val Pro Ile Trp Ile Thr Phe Asn Glu Pro Leu Leu Tyr
305                 310                 315                 320

Ser Phe Asn Phe Ala Gly Thr Asn Asn Val Val His Ala His Ala Gln
                325                 330                 335

Val Tyr His Phe Tyr His Asp Glu Leu Lys Ala Thr Gly Gln Ile Gly
            340                 345                 350

Ile Lys Phe Asn Asp Asn Phe Gly Val Pro Arg Asn Pro Lys Asn Ser
            355                 360                 365

Ser Asp Val Glu Ala Ala Asn Arg Phe Gln Glu Met Gln Leu Gly Leu
            370                 375                 380

Phe Ala Asn Pro Ile Phe Leu Gly Gln Gln Tyr Pro Asp Ser Ile Leu
385                 390                 395                 400

Met Thr Leu Pro Gly Ala Lys Pro Leu Gly Lys Gln Glu Leu Ser Tyr
                405                 410                 415

Ile Ala Asn Thr Ser Asp Phe Phe Gly Ile Asp Pro Tyr Thr Ala Thr
            420                 425                 430

Val Val Ser Gln Pro Ala Gly Gly Ile Asp Ala Cys Ala Ala Asn Pro
            435                 440                 445

```
Ser Val Ala Asn Ser Leu Phe Pro Tyr Cys Val Val Gln Glu Thr Lys
    450                 455                 460

Asn Ile Tyr Gly Trp Asn Ile Gly Tyr Arg Ser Gln Ser Tyr Val Tyr
465                 470                 475                 480

Ile Thr Pro Thr Tyr Leu Arg Glu Tyr Leu Asn Tyr Leu Trp Asn Thr
                485                 490                 495

Phe Arg His Pro Val Phe Val Thr Glu Phe Gly Phe Pro Val Phe Ala
            500                 505                 510

Glu Ala Glu Lys Glu Leu Ser Asp Gln Gln Phe Asp Ser Pro Arg Ser
        515                 520                 525

Ile Tyr Tyr Leu Ser Phe Met Ser Glu Ile Leu Lys Ala Ile His Glu
530                 535                 540

Asp Gly Val His Val Met Gly Ala Leu Ala Trp Ser Trp Ala Asp Asn
545                 550                 555                 560

Trp Glu Phe Gly Asp Tyr Ser Gln Gln Phe Gly Met Gln Val Val Asn
                565                 570                 575

Arg Thr Thr Gln Gln Arg Phe Tyr Lys Lys Ser Leu Phe Asp Leu Val
            580                 585                 590

Asp Phe Val Gly Ala Arg Ser Leu Ser Ser Asp Asn Gly Thr Val Ser
            595                 600                 605

<210> SEQ ID NO 4
<211> LENGTH: 1827
<212> TYPE: DNA
<213> ORGANISM: Talaromyces flavus

<400> SEQUENCE: 4
cagcaggtct acgtcaccac caccggctac accgacaggc cccagtgcac ccagctcgcc      60
tcgtcgcccc agtaccactt tcagcccttc agctacgccc tcgaggaaac cgtccgctac     120
gccaccagcg tgccctcgcc taccaccacg cgcacgtacg cccctccgta cagcagcgcc     180
gtcaagttcc tcaccacgtc gcccgccacc acgacctggg caactggct ccccggccag      240
acgctcatca ccgagactga cacgcacgac ccctacggcc aggccgcctg gtccagcctc     300
tggcagcagg tcgagcttga gaactacacc accacgggcc tctactggac caccgtcacg     360
cccacgcctg tgcctagcac cgacctcgtc ctgcctccgc gcgactactt cggccccacc     420
gactgctaca acttccccga cgacttcatc ttcggcgtcg ccggcagcgc cgctcaggtc     480
gagggcgccg tcgctctcga gggccgctcg ccgaccatcc tcgagaagct cgtcaacagc     540
tcgcagccca aggactacgt cacgaacgag aactactacc tctacaagca ggacatccag     600
cgcctcgccg ccatgggcgt caagtactac agcttcagca tcccctggac gcgcattctc     660
cccttttgtcc tgcctggcag ccccgtcaac caggaaggca tcaagcacta cgacgacctc     720
atcaacaccg tcctcgacgc cggcatgcag cccattgcca cgctcatcca cttcgacacg     780
ccctgggtct tgtcagcag cgacgagaac ttcacggctc ccccgacat cggctacaac      840
aacggcggct accagaacga gactttcgtc gacgcctacg tcaactacgc caagatcgtc     900
ctcagccact cgccgatcg cgtccccatc tggattacct caacgagcc cctcctctac      960
tccttcaact cgccggcac caacaacgtc gtccacgctc acgcccaggt ctaccacttc     1020
taccacgacg agctgaaggc caccggccag atcggcatca agttcaacga caactttggc     1080
gtccctcgca accccaagaa cagctccgac gtcgaggccg ccaaccgctt ccaagagatg     1140
cagctcggc tcttcgcgaa ccccatcttc ctcggccagc agtaccccga cagcatcctc     1200
atgacgctcc ctggcgccaa gcctctcggc aagcaagagc tgagctacat tgccaacacc    1260
```

```
agcgactttt tcggcattga ccctacacc gccaccgtcg tcagccagcc tgctggcgga    1320
atcgacgcct gcgctgcgaa ccctccgtc gccaactcgc tgttccccta ctgcgtcgtc    1380
caagaaacga agaacatcta cggctggaac attggctacc gcagccagag ctacgtctac    1440
atcaccccta cctacctccg cgagtacctc aactacctct ggaacacctt cgacaccccc    1500
gtgttcgtca ccgagttcgg cttccccgtc tttgccgagg ccgagaagga actcagcgac    1560
cagcagttcg actcgccccg cagcatctac tacctgagct tcatgagcga gatcctcaag    1620
gccatccacg aggacggcgt ccacgtcatg ggcgccctgg cctggtcctg ggccgacaac    1680
tgggagttcg cgactacag ccagcagttt ggcatgcagg ttgtcaaccg caccacgcag    1740
cagcgcttct acaagaagtc cctcttcgac ctggtcgact cgtcggcgc tcgctccctg    1800 agcagcgaca acggcaccgt cagctga                                        1827

<210> SEQ ID NO 5
<211> LENGTH: 603
<212> TYPE: PRT
<213> ORGANISM: Penicillium echinulatum

<400> SEQUENCE: 5
```

| Gln | Glu | Val | Tyr | Val | Thr | Thr | Thr | Gly | Tyr | Ser | Ala | Arg | Pro | Gln | Cys |
|---|---|---|---|---|---|---|---|---|---|---|---|---|---|---|---|
| 1 | | | | 5 | | | | | 10 | | | | | 15 | |

| Thr | Gln | Ser | Asn | Val | Thr | Pro | Lys | Tyr | His | Phe | Gln | Pro | Phe | Ser | Tyr |
|---|---|---|---|---|---|---|---|---|---|---|---|---|---|---|---|
| | | | 20 | | | | | 25 | | | | | 30 | | |

| Thr | Leu | Asn | Glu | Thr | Val | Arg | Tyr | Ala | Thr | Ser | Val | Pro | Ser | Pro | Thr |
|---|---|---|---|---|---|---|---|---|---|---|---|---|---|---|---|
| | | | 35 | | | | | 40 | | | | | 45 | | |

| Thr | Thr | Arg | Lys | Tyr | Ala | Ala | Pro | Tyr | Thr | Asp | Val | Lys | His | Leu |
|---|---|---|---|---|---|---|---|---|---|---|---|---|---|---|
| | 50 | | | | | 55 | | | | | 60 | | | |

| Thr | Thr | Ser | Trp | Ser | Thr | Ser | Thr | Trp | Gly | Ser | Trp | Val | Pro | Asp | Gln |
|---|---|---|---|---|---|---|---|---|---|---|---|---|---|---|---|
| 65 | | | | | 70 | | | | | 75 | | | | | 80 |

| Thr | Ser | Ile | Ser | Ala | Thr | Asp | Thr | Lys | Asp | Pro | Tyr | Gly | Gln | Ala | Ala |
|---|---|---|---|---|---|---|---|---|---|---|---|---|---|---|---|
| | | | | 85 | | | | | 90 | | | | | 95 | |

| Trp | Ser | Ser | Met | Trp | Leu | Gln | Ala | Asp | Leu | His | Asn | Tyr | Thr | Thr | Thr |
|---|---|---|---|---|---|---|---|---|---|---|---|---|---|---|---|
| | | | 100 | | | | | 105 | | | | | 110 | | |

| Gly | Leu | Phe | Ser | Thr | Thr | Val | Ser | Pro | Thr | Pro | Val | Pro | Ser | Ser | Glu |
|---|---|---|---|---|---|---|---|---|---|---|---|---|---|---|---|
| | | | 115 | | | | | 120 | | | | | 125 | | |

| Leu | Val | Leu | Pro | Pro | Arg | Asp | Tyr | Phe | Gly | Pro | Thr | Asp | Cys | Tyr | Asn |
|---|---|---|---|---|---|---|---|---|---|---|---|---|---|---|---|
| | 130 | | | | | 135 | | | | | 140 | | | | |

| Phe | Pro | Gln | Asp | Phe | Val | Phe | Gly | Val | Ala | Gly | Ser | Ala | Ala | Gln | Ile |
|---|---|---|---|---|---|---|---|---|---|---|---|---|---|---|---|
| 145 | | | | | 150 | | | | | 155 | | | | | 160 |

| Glu | Gly | Ala | Ile | Gly | Leu | Asp | Gly | Arg | Gly | Pro | Ser | Leu | Leu | Glu | Lys |
|---|---|---|---|---|---|---|---|---|---|---|---|---|---|---|---|
| | | | | 165 | | | | | 170 | | | | | 175 | |

| Leu | Val | Ser | Asp | Asp | Lys | Pro | Lys | Asp | Tyr | Val | Thr | Asn | Glu | Asn | Tyr |
|---|---|---|---|---|---|---|---|---|---|---|---|---|---|---|---|
| | | | 180 | | | | | 185 | | | | | 190 | | |

| Phe | Leu | Tyr | Lys | Gln | Asp | Ile | Gln | Arg | Leu | Ala | Ala | Met | Gly | Val | Glu |
|---|---|---|---|---|---|---|---|---|---|---|---|---|---|---|---|
| | | | 195 | | | | | 200 | | | | | 205 | | |

| Tyr | Tyr | Ser | Phe | Thr | Ile | Pro | Trp | Thr | Arg | Ile | Leu | Pro | Phe | Ala | Leu |
|---|---|---|---|---|---|---|---|---|---|---|---|---|---|---|---|
| | 210 | | | | | 215 | | | | | 220 | | | | |

| Pro | Gly | Thr | Pro | Val | Asn | Gln | His | Gly | Ile | Asp | His | Tyr | Asn | Asp | Leu |
|---|---|---|---|---|---|---|---|---|---|---|---|---|---|---|---|
| 225 | | | | | 230 | | | | | 235 | | | | | 240 |

| Ile | Asp | Thr | Val | Leu | Asp | Ala | Gly | Met | Thr | Pro | Val | Val | Thr | Met | Leu |
|---|---|---|---|---|---|---|---|---|---|---|---|---|---|---|---|
| | | | | 245 | | | | | 250 | | | | | 255 | |

| His | Phe | Asp | Ser | Pro | Leu | Met | Phe | Val | Ala | Ser | Asp | Asn | Ile | Thr | Lys |
|---|---|---|---|---|---|---|---|---|---|---|---|---|---|---|---|
| | | | 260 | | | | | 265 | | | | | 270 | | |

His Pro Asp Ile Gly Tyr Asn Asn Gly Gly Tyr Gln Asn Glu Thr Phe
            275                 280                 285

Val Asp Ala Phe Val Asn Tyr Gly Lys Val Leu Leu Ser His Tyr Ala
    290                 295                 300

Asp Arg Val Pro Ile Trp Val Thr Phe Asn Glu Pro Leu Leu Tyr Ala
305                 310                 315                 320

Phe Asn Phe Lys Gly Ala Asp Asn Val Val Lys Ala His Ala Gln Val
                325                 330                 335

Tyr His Phe Tyr His Asp Thr Leu Lys Ala Thr Gly Lys Ile Gly Ile
            340                 345                 350

Lys Phe Asn Asp Asn Phe Gly Val Pro Lys Asp Pro Lys Asn Ser Ser
            355                 360                 365

His Val Leu Ala Ala Asp Arg Phe Gln Glu Met Gln Leu Gly Ile Phe
    370                 375                 380

Ala Asn Pro Ile Phe Leu Gly Lys Gln Tyr Pro Lys Ser Val Leu Asp
385                 390                 395                 400

Thr Leu Pro Gly Ala Lys Pro Leu Ser Lys Ser Glu Leu Lys His Ile
                405                 410                 415

His Asn Thr Ser Asp Phe Phe Gly Ile Asp Pro Tyr Thr Ala Thr Val
            420                 425                 430

Val Ser Pro Ala Asn Glu Gly Ile Glu Ala Cys Ala Ala Asn Gln Ser
    435                 440                 445

Ser Ser Asn Glu Leu Phe Pro Tyr Cys Val Lys Gln Glu Thr Lys Asn
    450                 455                 460

Val Tyr Gly Trp Asn Ile Gly Tyr Arg Ser Glu Ser Tyr Val Tyr Ile
465                 470                 475                 480

Thr Pro Thr His Phe Arg Glu Tyr Leu Phe Tyr Leu Trp Asn Thr Phe
                485                 490                 495

Arg Ser Pro Ile Leu Val Ser Glu Phe Gly Phe Pro Val His Ala Glu
            500                 505                 510

Ala Glu Ser Glu Glu Leu Ser Asp Gln Leu Phe Asp Ser Pro Arg Ser
    515                 520                 525

Val Tyr Tyr Leu Ser Phe Met Ser Glu Ile Leu Lys Ser Ile Tyr Glu
    530                 535                 540

Asp Gly Val His Val Met Gly Ala Leu Ala Trp Ser Phe Val Asp Asn
545                 550                 555                 560

Trp Glu Phe Gly Asp Tyr Thr Gln Gln Phe Gly Ile Gln Ala Val Asn
                565                 570                 575

Arg Thr Thr Gln Gln Arg Tyr Tyr Lys Lys Ser Phe Phe Asp Leu Val
            580                 585                 590

Asp Phe Val Lys Thr Arg Gln Pro Asn Lys Asp
            595                 600

<210> SEQ ID NO 6
<211> LENGTH: 1812
<212> TYPE: DNA
<213> ORGANISM: Penicillium echinulatum

<400> SEQUENCE: 6
caagaggtct acgtcaccac caccggctac agcgcccgac ctcagtgcac ccagagcaac    60
gtcacgccca gtaccacttt cagcccttc agctacaccc tcaacgagac tgtccgctac    120
gccaccagcg tgcctcgcc taccaccacg cgcaagtacg ccgctcctta caccgacgtc    180
gtcaagcacc tcaccacctc gtggtccacc agcacctggg gcagctgggt ccccgaccag    240

```
accagcatca gcgccaccga cacgaaggac ccctacggcc aggccgcctg gtccagcatg    300
tggctccagg ccgacctcca caactacacc accacgggcc tcttcagcac cacggtcagc    360
cccacgcctg tgcctagcag cgagctggtc ctgcctcctc gcgactactt cggccccacc    420
gactgctaca actttcccca ggacttcgtc tttggcgtcg ccggcagcgc cgctcagatc    480
gagggcgcca tcggcctcga cggacgcggc cctagcctcc tcgagaagct cgtcagcgac    540
gacaagccca aggactacgt gaccaacgag aactacttcc tctacaagca ggacatccag    600
cgcctcgccg ccatgggcgt cgagtactac agcttcacga tccctggac gcgcattctc    660 cccttcgctc tccccggcac gcccgtcaac cagcacggca tcgaccacta caacgacctc    720
atcgacaccg tcctcgacgc cggcatgacg cccgtcgtca ccatgctcca cttcgactcg    780
cccctcatgt tcgtcgccag cgacaacatc acgaagcacc ccgacatcgg ctacaacaac    840
ggcggctacc agaacgagac tttcgtcgac gccttcgtca actacggcaa ggtcctcctc    900
agccactacg ccgatcgcgt ccccatctgg gtgaccttca acgagcccct cctctacgcc    960
ttcaacttca agggcgccga caacgtcgtg aaggcccacg ctcaggtcta ccacttctac   1020
cacgacaccc tgaaggccac cggcaagatc ggcatcaagt tcaacgacaa cttcggcgtc   1080
cccaaggatc ccaagaacag cagccacgtc ctggccgccg accgcttcca agagatgcag   1140
ctcggcatct tcgcgaaccc catcttcctc ggcaagcagt accccaagag cgtcctggac   1200
accctgcctg gcgccaagcc tctcagcaag agcgagctga agcacatcca caacaccagc   1260 gacttttcg gcattgaccc ctacaccgcc accgtcgtca gccccgccaa cgagggcatc   1320
gaggcctgcg ccgccaacca gagcagcagc aacgagctgt tcccctactg cgtcaagcaa   1380
gaaacgaaga acgtctacgg ctggaacatt ggctaccgca gcgagagcta cgtctacatc   1440
acgcccacgc acttccgcga gtacctcttc tacctctgga acacctttcg cagccccatc   1500
ctggtcagcg agttcggctt ccccgtccac gccgaggccg agagcgagga actcagcgac   1560
cagctgttcg acagccctcg cagcgtctac tacctcagct tcatgagcga gatcctcaag   1620
agcatctacg aggacggcgt ccacgtcatg ggcgccctgg cctggtcgtt cgtcgacaac   1680
tgggagttcg gcgactacac ccagcagttc ggcatccagg ccgtcaaccg aaccacgcag   1740
cagcggtact acaagaagtc cttcttcgac ctcgtcgact tcgtcaagac ccgccagccg   1800
aacaaggact ga                                                       1812
```

<210> SEQ ID NO 7
<211> LENGTH: 17
<212> TYPE: PRT
<213> ORGANISM: Trichoderma reesei

<400> SEQUENCE: 7

Met Tyr Arg Lys Leu Ala Val Ile Ser Ala Phe Leu Ala Thr Ala Arg
1               5                   10                  15

Ala

BETA GLUCOSIDASE WITH HIGH GLUCOSE TOLERANCE, HIGH THERMAL STABILITY AND BROAD PH ACTIVITY SPECTRUM

PRIORITY

This application is a U.S. national application of the international application number PCT/FI2019/050423 filed on Jun. 4, 2019 and claiming priority of Finnish application number 20185511 filed on Jun. 5, 2018 the contents of all of which are incorporated herein by reference.

REFERENCE TO A SEQUENCE LISTING

This application contains a sequence listing as an ASCII text file identified by the file name "Sequence_listing_PI100853.txt" created on Nov. 16, 2020 and having a size of 23.0 kb, which is hereby incorporated herein by reference.

FIELD OF THE INVENTION

The present application relates to a polypeptide having beta-glucosidase activity, polynucleotides and nucleic acid constructs encoding those polypeptides and compositions comprising such polypeptides. The application also relates to methods of producing such polypeptides and hosts for production. In addition, the invention relates to a method of hydrolysing biomass, a method for synthesis of oligosaccharides and/or aryl-glycosides and/or alkyl-glycosides and a use of the polypeptide here described in hydrolysis or synthesis of glycosides.

BACKGROUND

β-glucosidases (beta-D-glucoside glucohydrolase, EC 3.2.1.21) cleave the beta-glycosidic linkages in di- and oligo-glucosaccharides and several other glycoconjugates to release non-reducing terminal glycosyl residues, glycoside and oligosaccharides. Typical microbial beta-glucosidases show broad substrate specificity and they can hydrolyse a wide range of substrates with different bonds such as β(1→4), β(1→3), β(1→6), α(1→4), α(1→3), and α(1→6) linkage. Beta-glucosidases have been classified into glycoside hydrolase (GH) families GH1, GH3, GH5, GH9, GH30 and GH116 based on their amino acid sequences. Most β-glucosidases belonging to GH1 family are predominately intracellular enzymes.

β-glucosidase have several industrial applications. They are involved in cellulolytic enzyme mixtures for fuels and chemicals production from lignocellulosic materials. Beta-glucosidases are also employed in industry for hydrolysis of bitter compounds during juice extraction and liberation of aroma from wine grapes. In flavor industry, beta-glucosidases are the key enzymes in the enzymatic release of aromatic compounds from glucosidic precursors present in fruits and fermenting products.

Lignocellulose is an abundant and renewable biomaterial usable for production bioethanol, biofuels and other bio-based components for industry. A proper saccharification is needed for efficient and economic production of biofuels and providing monomers for other bio-based components.

β-glucosidases are also used in food processing and as a flavor enzyme to enhance the flavor of wine, tea and fruit juice. Beta-Glucosidases play an important role in flavor liberation from glucosylated (β-glucosides conjugated) precursors in fruits and other plant tissues. Cleavage of phenolic and phytoestrogen glucosides from fruits and vegetables is also carried out by applying this enzyme to extract medicinally important compounds and to enhance the quality of beverages. Beta-glucosidases can improve the organoleptic properties of citrus fruits.

In addition to several hydrolytic applications, beta-glucosidases can be used in synthesis of stereo- and regiospecific glycosides or oligosaccharides, which are in turn potentially useful as functional materials, nutraceuticals, or pharmaceuticals because of their biological recognition, signalling mechanisms, and antibiotic properties. Furthermore, beta-glucosidases can be used to synthetise disaccharides, such as sophorose or gentiobiose to act as inducers of cellulase synthesis in fungi. Some beta-glucosidases can also synthetise xylobiose or xylotriose that act as inducers for hemicellulase synthesis in fungi.

WO 2014059541 discloses enzymes having activities relating to biomass processing and/or degradation and *T. aurantiacus* enzyme having beta-glucosidase activity. WO 2013181760 discloses enzymes having activities relating to biomass processing and/or degradation and *Aureobaisdium pullulanse* enzyme having beta-glucosidase activity.

There is thus a continuous a need for novel β-glucosideses suitable for industrial use and production.

SUMMARY

An aspect of the invention is a polypeptide having beta-glucosidase activity. Characteristic features of said polypeptide are given in claim 1.

Another aspect of the invention is an isolated polynucleotide. Characteristic features of said polynucleotide are given in claim 5.

Another aspect of the invention is a nucleic acid construct. Characteristic features of said nucleic acid construct are given in claim 6.

Another aspect of the invention is a recombinant host. Characteristic features of said host are given in claim 7.

Another aspect of the invention is a composition. According to the invention said composition comprises the polypeptide here described.

Another aspect of the invention is a method of producing the polypeptide here described.

According to the invention said method comprises steps of
 a. cultivating the recombinant host of claim 6 under conditions conducive for production of the polypeptide; and
 b. recovering the polypeptide.

Another aspect of the invention is a method of hydrolysing biomass. According to the invention said method comprises steps of contacting said biomass with the polypeptide described here or a composition described here.

Another aspect of the invention is a method for synthesis of oligosaccharides and/or aryl-glycosides and/or alkyl-glycosides. According to the invention said method comprises steps of contacting carbohydrate material with the polypeptide described here or a composition described here.

Another aspect of the invention is a use of the polypeptide here described in hydrolysis or synthesis of glycosides.

The main embodiments are characterized in the independent claims. Further embodiments are disclosed in the dependent claims and the description. The features recited in dependent claims and in the embodiments are mutually freely combinable unless otherwise explicitly stated.

BRIEF DESCRIPTION OF THE FIGURES

FIG. 5 shows a sequence alignment of mature polypeptides here described; CLUSTAL O (1.2.4) multiple sequence alignment of the mature polypeptides (pairwise identity 76.9-78.1%), predicted catalytic domain is in bold (pairwise identity 78.4-81.3%; N-terminal domain: 1-144; Catalytic domain: 145-589).

DEPOSITS

Figure 1:
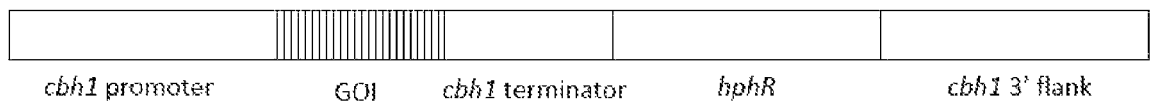
FIG. 1 shows the design of the expression cassette for expression of the beta-glucosidases. GOI=gene of interest hphR=selection for hygromycine resistance.

The following strain depositions according to the Budapest Treaty on the International Recognition of Deposit of Microorganisms for the Purposes of Patent Procedure were made at the VTT Culture Collection, P.O. Box 1000 (Tietotie 2), FI-02044 VTT, Finland: *Penicilliopsis clavariiformis* assigned accession number VTT-D-03941 and *Penicillium echinulatum* assigned accession number VTT-D-92031 were deposited on 26 Feb. 2018.

TABLE 1

List of sequences used here

| SEQ ID NO | Description |
| --- | --- |
| 1 | mature GH1-polypeptide from *Penicilliopsis clavariiformis* (Pc) |
| 2 | coding sequence of Pc_GH1; codon optimized for *T. reesei* |
| 3 | mature GH1-polypeptide from *Talaromyces flavus* (Tf) |
| 4 | coding sequence of Tf_GH1; codon optimized for *T. reesei* |
| 5 | mature GH1-polypeptide from *Penicillium echinulatum* (Pe) |
| 6 | coding sequence of Pe_GH1; codon optimized for *T. reesei* |
| 7 | signal sequence of CBHI |

DETAILED DESCRIPTION

Usually the rate-limiting enzyme of cellulase mixtures for biomass hydrolysis is β-glucosidase catalysing hydrolysis of cellobiose to glucose (monosaccharide). In addition to the relative low amount of said activity in typical cellulase mixtures, it is also inhibited by the end-product glucose. The aim was to develop novel polypeptides having β-glucosidase activity also in presence of glucose. In addition, said polypeptides should preferably be secretable by the production host, be suitable for industrial production and show at least moderate thermotolerance. The inventors were able to find three novel polypeptides maintaining their catalytic activity in increased glucose concentration.

The present invention relates to a polypeptide having beta-glucosidase activity, comprising or consisting of:
 a. a polypeptide having at least 84% identity to the sequence of mature polypeptide of SEQ ID NO: 1 [Pc_GH1]; or
 b. a polypeptide encoded by the nucleotide that hybridizes under high stringent conditions with the complement of the sequence encoding the mature polypeptide defined by SEQ ID NO: 1; or
 c. a fragment or a variant of the polypeptide of (a) or (b) having beta-glucosidase activity.

In one embodiment the mature polypeptide of SEQ ID NO: 1 has at least 85% identity, preferably at least 90% identity, more preferably at least 95% identity, at least 97% identity, at least 98% identity at least 99% identity, and most preferably 99.8% identity to the sequence of mature polypeptide comprising or consisting of SEQ ID NO: 1.

The present invention relates to a polypeptide having beta-glucosidase activity, comprising or consisting of:
a. a polypeptide having at least 80% identity to the sequence of mature polypeptide of SEQ ID NO: 3 [Tf_GH1]; or
b. a polypeptide encoded by the nucleotide that hybridizes under high stringent conditions with the complement of the sequence encoding the mature polypeptide defined by SEQ ID NO: 3; or
c. a fragment or a variant of the polypeptide of (a) or (b) having beta-glucosidase activity.

In one embodiment the mature polypeptide of SEQ ID NO: 3 has at least 90% identity, preferably at least 95% identity, more preferably at least 97% identity or at least 99% identity, and most preferably 99.8% identity to the sequence of mature polypeptide comprising or consisting of SEQ ID NO: 3.

The present invention relates to a polypeptide having beta-glucosidase activity, comprising or consisting of:
a. a polypeptide having at least 80% identity to the sequence of mature polypeptide of SEQ ID NO: 5 [Pe_GH1]; or
b. a polypeptide encoded by the nucleotide that hybridizes under high stringent conditions with the complement of the sequence encoding the mature polypeptide defined by SEQ ID NO: 5; or
c. a fragment or a variant of the polypeptide of (a) or (b) having beta-glucosidase activity.

In one embodiment the mature polypeptide of SEQ ID NO: 5 has at least 90% identity, preferably at least 95% identity, more preferably at least 97% identity or at least 99% identity, and most preferably 99.8% identity to the sequence of mature polypeptide comprising or consisting of SEQ ID NO: 5.

Figure 3:
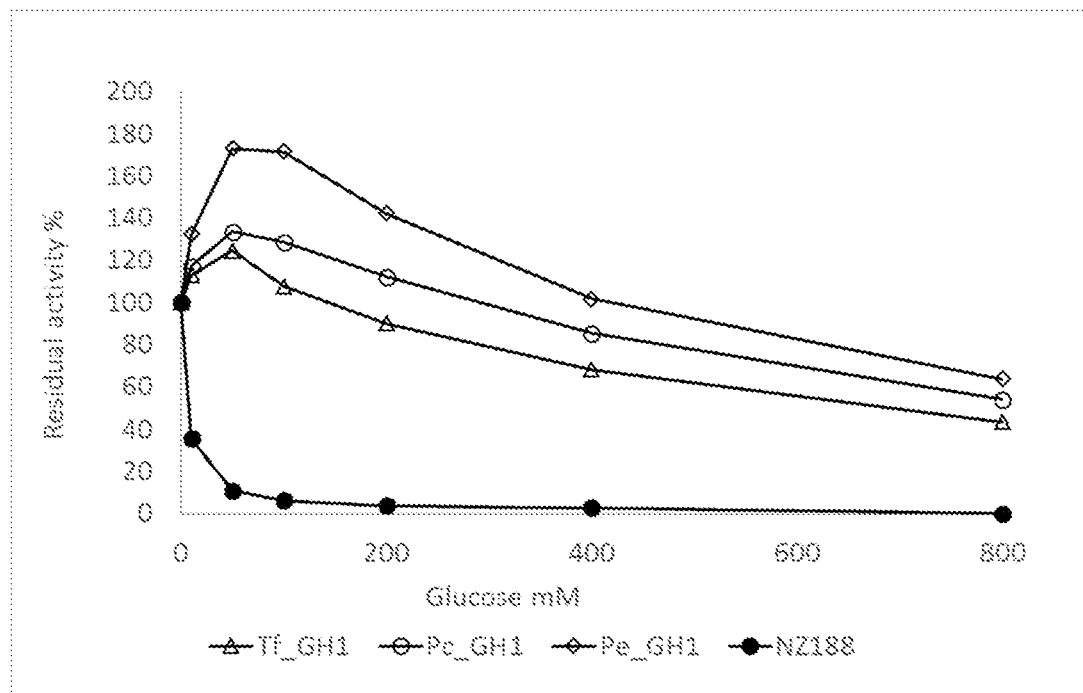
FIG. 3 shows the glucose tolerance of three novel beta-glucosidases. The activity of the beta-glucosidases was measured using pNPG as a substrate, in the presence of 0-800 mM glucose at pH 5. The results are presented as %-residual activities, that were calculated as follows: (activity in presence of n mM of glucose)/(activity in presence of 0 mM glucose)×100.

It was surprisingly found that the above polypeptides maintain their catalytic activity in elevated glucose concentrations. The catalytic activity of said polypeptides was tested in various glucose concentrations and compared to bench mark commercial enzyme product. The polypeptide Pc_GH1 retained full activity at 200 mM glucose concentration, the polypeptide Tf_GH1 at 100 mM glucose concentration and the polypeptide Pe_GH1 at 400 mM glucose concentration. At the above-mentioned glucose concentrations the activity of the commercial reference was 3-6% of the activity measured in absence of glucose. The result of the study is shown in FIG. 3.

In one embodiment of the invention the mature β-glucosidase polypeptide from Penicilliopsis clavariiformis (Pc_GH1) here described maintains at least 70%, preferably at least 80%, more preferably at least 90% and most preferably at least 95% of its catalytic activity at glucose concentration of 200 mM when compared to measurement in respective conditions but without glucose.

In one embodiment of the invention the mature β-glucosidase polypeptide Pc_GH1 here described maintains at least 60%, preferably at least 70% and most preferably at least 80%, at glucose concentration of 400 mM when compared to measurement in respective conditions but without glucose.

In one embodiment of the invention the mature β-glucosidase polypeptide Pc_GH1 here described maintains at least 30%, more preferably at least 40% and most preferably at least 50%, its catalytic activity at glucose concentration of 800 mM when compared to measurement in respective conditions but without glucose.

In one embodiment of the invention the mature β-glucosidase polypeptide from Talaromyces flavus (Tf_GH1) here described maintains at least 70%, preferably at least 80% and most preferably at least 90% of its catalytic activity at glucose concentration of 200 mM when compared to measurement in respective conditions but without glucose.

In one embodiment of the invention the mature β-glucosidase polypeptide Tf_GH1 here described maintains at least 40%, preferably at least 50%, and most preferably at least 60% of its catalytic activity at glucose concentration of 400 mM when compared to measurement in respective conditions but without glucose.

In one embodiment of the invention the mature β-glucosidase polypeptide Tf_GH1 here described maintains at least 20%, preferably at least 30% and most preferably at least 40% of its catalytic activity at glucose concentration of 800 mM when compared to measurement in respective conditions but without glucose.

In one embodiment of the invention the mature β-glucosidase polypeptide from Penicillium echinulatum (Pe_GH1) here described maintains at least 70%, preferably at least 80%, more preferably at least 90% and most preferably at least 95% of its catalytic activity at glucose concentration of 200 mM when compared to measurement in respective conditions but without glucose.

In one embodiment of the invention the mature β-glucosidase polypeptide Pe_GH1 here described maintains at least 70%, preferably at least 80%, more preferably at least 90% and most preferably at least 95%, of its catalytic activity 400 mM when compared to measurement in respective conditions but without glucose.

In one embodiment of the invention the mature β-glucosidase polypeptide Pe_GH1 here described maintains at least 40%, preferably at least 50%, and most preferably at least 60%, its catalytic activity at glucose concentration of 800 mM when compared to measurement in respective conditions but without glucose.

Glucose tolerance is a remarkable advantage especially in hydrolysis applications where high glucose concentrations are present (e.g. saccharification of biomass in high substrate consistency, processing of fruit products and beverages). On the other hand, glucose-tolerant beta-glucosidases can exhibit high rate of transglycosylation that can be employed in synthesis applications.

Figure 4:
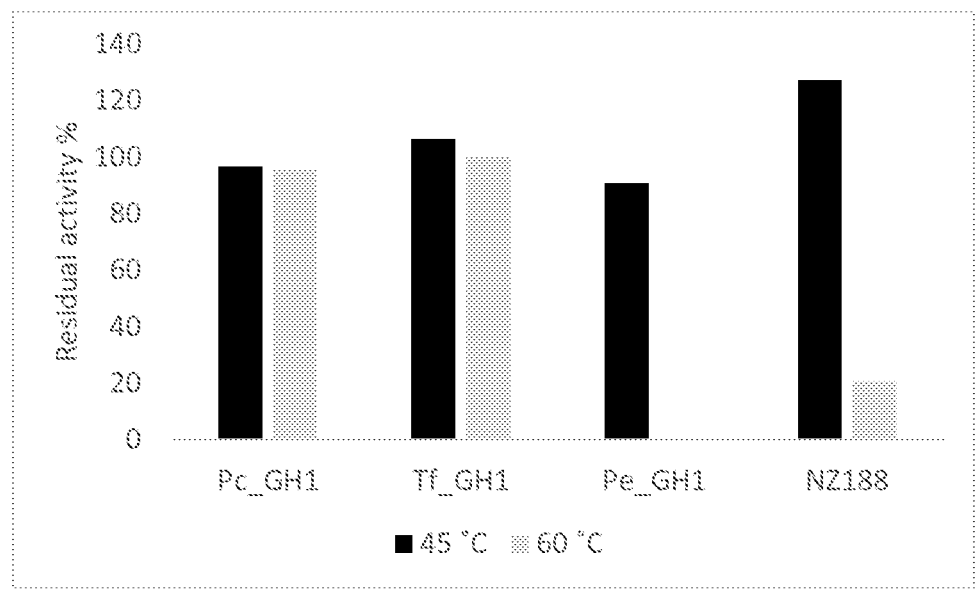
FIG. 4 shows the thermostability of three novel beta-glucosidases and the reference enzymes. The residual activity was measured using pNPG as a substrate, after incubating the enzyme samples for 21 h at 45° C. or 60° C., at pH 5. 100% is the activity of the samples preincubated at 4° C. before assaying on pNPG at 50° C., pH 5.

In addition, it was surprisingly found that mature β-glucosidase polypeptides from Penicilliopsis clavariiformis (Pc_GH1) and Talaromyces flavus (Tf_GH1) here described are able to maintain their catalytic activity in elevated temperatures up to 60° C. for several hours. The result of the study is shown in FIG. 4.

In one embodiment of the invention the mature β-glucosidase polypeptides Pc_GH1 and Tf_GH1 here described maintain at least 90% and most preferably at least 95% of its catalytic activity during incubation of 21 hours at 45° C. as compared to a catalytic activity of sample incubated in respective conditions at 4° C.

In one embodiment of the invention the mature β-glucosidase polypeptides Pc_GH1 and Tf_GH1 here described maintain at least 90% and most preferably at least 95% of its catalytic activity during incubation of 21 hours at 60° C. as compared to a catalytic activity of sample incubated in respective conditions at 4° C.

In one embodiment of the invention the mature β-glucosidase polypeptides Pc_GH1 and Tf_GH1 here described maintain at least 70%, preferably at least 80%, more preferably at least 90% and most preferably at least 95% of its catalytic activity during incubation of 20 hours at 60° C. as compared to a catalytic activity of sample incubated in respective conditions at 4° C.

In one embodiment of the invention the mature β-glucosidase polypeptides Pc_GH1 here described maintains its catalytic activity during incubation of 2 hours at 65° C. at pH 5. In one embodiment of the invention the mature β-glucosidase polypeptides Pc_GH1 here described maintains at least 10%, preferably at least 20% of its catalytic activity during incubation of 2 hours at 70° C. at pH 5. In one embodiment of the invention the mature β-glucosidase polypeptides Pc_GH1 here described is inactivated during incubation of 2 hours at 75° C. at pH 5. In this connection inactivation means that less than 5% of catalytic activity is maintained after incubation at 75° C. or higher temperature. For experimental results, see FIG. 6.

In industrial processes tolerance to elevated temperatures is usually an advantage as the catalytic efficiency increases at higher temperatures and inhibitor tolerance is relieved. The risks of microbial contaminations is also decreased. Thermostable enzyme can also be more flexibly applied in industrial processes where maintenance of high temperature is prerequisite or economically feasible. Thermal stability of enzyme can indicate overall structural stability in presence denaturing substances, such as detergents and organic solvents, which allows their use in non-aqueous reaction media. Especially in food, feed and beverage application it may beneficial that the activity of the enzyme can be inactivated without need of using extreme temperatures or prolonged heating times, which could be harmful to nutritional components and flavor agents.

The mature β-glucosidase polypeptide Pc_GH1 here described has a good pH stability at pH ranging between at least 3.0 to 6.5. This is an advantage in applications requiring low pH, broad range allows flexibility to processing conditions. An example within food, feed and beverage field is processing berries and fruits. FIGS. 7 to 10 demonstrate the advantage also over prior art β-glucosidases.

In one embodiment of the invention the mature β-glucosidase polypeptide Pc_GH1 here described maintains at least 40%, preferably at least 50% of its relative catalytic activity at pH 3 to 5.5. In one embodiment of the invention the mature β-glucosidase polypeptide Pc_GH1 here described maintains at least 80% of its relative catalytic activity at pH 3.5 to 5.5.

In one embodiment of the invention the mature β-glucosidase polypeptide Pc_GH1 here described maintains at least 80%, preferably at least 90% of its catalytic activity at ethanol concentration of 5 to 20 vol-% when compared to measurement in respective conditions but without ethanol. In one embodiment of the invention the mature β-glucosidase polypeptide Pc_GH1 here described maintains at least 100% of its catalytic activity at ethanol concentration of 5 to 20 vol-% when compared to measurement in respective conditions but without ethanol. In one embodiment of the invention the mature β-glucosidase polypeptide Pc_GH1 here described maintains at least 20%, preferably at least 30%, more preferably at least 40% of its catalytic activity at ethanol concentration of 40 vol-% when compared to measurement in respective conditions but without ethanol. In one embodiment of the invention the mature β-glucosidase polypeptide Pc_GH1 here described maintains at least 50%, preferably even at least 60% of its catalytic activity at ethanol concentration of 40 vol-% when compared to measurement in respective conditions but without ethanol.

Tolerance to ethanol is an advantage in manufacturing alcoholic beverages. In such applications β-glucosidases can be used for example in liberating aromatic substances. Fungal enzymes can be naturally intra- or extracellular, and in latter case bound to the cell wall or soluble. The enzymes are adapted to function in their natural environment. Heterologous production and protein product collection of naturally soluble extracellular enzymes in industrial production host is more straightforward than in the case of intracellular enzymes, which can reduce the production costs and increase the protein yield. The adaptation of the enzyme to function in changing surroundings of the fungus can provide industrially beneficial properties to the enzyme, e.g. stability, flexible pH range.

Thus, the polypeptides described here are suitable to be produced as soluble extracellular enzymes using secretion signal. Said secretion signal may the natural secretion signal of the polypeptide derived from the source strain, it may be a secretion signal from the production host, or any other secretion signal including secretion signals from other strains (other than source of original beta-glucosidase polypeptide sequence or other than production host) and also a synthetic secretion signal.

Said polypeptide may be an isolated polypeptide. The term "isolated" as used here means that the material has been removed from its original environment (e.g., the natural environment. Secreted polypeptides are deemed to be isolated as not anymore within the secreting host or production organism. The beta-glucosidases here describes can encoded by a nucleic acid comprising also a secretion signal.

A term "identity," as used interchangeably here means a sequence similarity between two polypeptide or polynucleotide sequences. The degree of identity is determined by using EMBOSS Water pairwise sequence alignment program at EBI (European Bioinformatics Institute) with the following parameters: BLOSUM62, Gap open 10, Gap extend 0.5. The algorithm is described in Smith and Waterman (1981).

As used here 'stringent hybridization compositions' mean an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

In one embodiment said fragment comprises or consists of amino acids residues in positions 145-602 of Pc_GH1 of SEQ ID NO: 1, 145-609 of Tf_GH1 of SEQ ID NO: 3 or 145-603 of GH_Pe_GH1 of SEQ ID NO: 5.

An expression 'a derivative of a polypeptide' means polypeptides comprising one or more amino acid substitutions with a conserved or non-conserved amino acid residue or one or more insertions or deletions to the mature polypeptide. A person skilled in the art understands that modifications within conserved regions are more likely to effect on activity of the polypeptide. FIG. 5 shows a multiple sequence alignment (CLUSTAL O (1.2.4)) of the mature polypeptides (lacking the secretion signal peptides) here described (pairwise identity 76.9-78.1%), predicted catalytic domain is shown in bold, amino acid residues 145-589; amino acid residues 1-144 represent N-terminal domain Pairwise identities of the mature polypeptides lacking the N-terminal domains are 78.4-81.3%.

An expression 'a fragment or a variant of the polypeptide having beta-glucosidase activity.' as used here means that said fragment or variant has at least 80%, preferably at least at least 90% of activity of the full length mature peptide analyzed in the same conditions.

The present invention relates to an isolated polynucleotide encoding the polypeptide of here described and claimed. Said polynucleotide may be an isolated polynucleotide. Any synthetic/artificial polynucleotide is deemed isolated.

The present invention relates to a nucleic acid construct comprising the polynucleotide here described operably linked to one or more control sequences directing the production of the polypeptide in a production host.

An expression "operably linkage" means that a polynucleotide is placed into a functional relationship with another nucleic acid sequence, such as promoter, enhancer, terminator localisation signal, secretion signal, secretion carrier.

As used herein, the term "nucleic acid construct" (includes also expression vectors, expression cassette and plasmids) means a nucleic acid construct usable for introducing genetic material into a host. Said construct carries at least the nucleic acid encoding the protein of interest and usually also at least a promoter. Said construct may incorporate heterologous nucleic acids into the genome of the host or e.g. act in an independently replicating plasmid. Prokaryotic and eukaryotic expression vectors are known within the art and commercially available. A person skilled in the art is able to elect suitable means for introducing and expressing the polynucleotide in the desired host.

The expression constructs here described may contain a selectable marker(s) which allow selection of transformed cells. A person skilled in the art is able to select suitable selection markers for the desired host. The codon usage of the polynucleotide and/or the nucleic acid construct may be optimized for a desired production host to ensure high expression of the gene and production of the protein of interest.

The present invention relates to a recombinant host comprising the polynucleotide here described (polynucleotide having β-glucosidase activity) operably linked to one or more control sequences directing the production of the polypeptide in said host or the nucleic acid construct here described.

Expression "recombinant host" as used here means that said host is genetically modified. Genetical modification may be done for example by introducing a nucleic acid sequence encoding a protein of interest (POI) such as β-glucosidase (optionally exogenous for said host) and/or nucleic acids enhancing the replication, and/or transcription or transcription and translation (expression) of the expression of the protein of interest (either endogenous of exogenous for said host). The nucleic acid may be introduced in a plasmid or as an expression construct/cassette. It may be a self-replicating plasmid or construct, or it may be integrated into the genome of said host.

In one embodiment the host is modified to over-express the polynucleotide encoding a polypeptide here described, wherein said polynucleotide being endogenous to said host. In one embodiment the host is modified the polynucleotide or the nucleic acid construct of here described is stably introduced into said host. Stable introduction of the expression construct to the host can be obtained using expression cassettes that are integrated into the host genome. Alternatively, autonomously replicating telomeric or plasmid expression vectors can be used.

The host may be a fungal cell, yeast cell or a bacterial cell. Suitable fungal cells without restricting to those are especially filamentous fungi cells, such as *Aspergillus, Trichoderma, Fusarium, Chrysosporium, Penicillium, Humicola,* *Neurospora, Myceliophthora thermophile*. In one embodiment said host is *T. reesei*. Filamentous fungi are natural producer of cellulolytic activities and widely used production host.

Suitable bacterial cells without restricting to those are *Escherichia coli, Lactococcus lactis* and *Bacillus subtilis*.

Suitable yeast cells without restricting to those are *Saccharomyces cerevisiae, Pichia pastoris, Yarrowia lipolytica,* and *Klyvuromyces lactis*.

The host may genetically modified. Typical modifications are deletions of degradative activities (such as proteases) or side activities (such as other cellulolytic activities of filamentous fungi) and modifications of expression locus.

The present invention relates to a composition comprising at least one the polypeptide here described.

The composition as simplest may be so called "whole culture broth" composition comprising the spent culture medium and production host, optionally after inactivating said host. The production host may be removed from spent culture medium by known means such as filtration. In addition, the enzymatic activity (activities) may be purified using known methods. In addition to β-glucosidase activity the composition may have one or more further enzymatic activities as side activities or activities beneficial for the application (e.g. cellulase mixture for hydrolysis). Degree of purity depend on the field of application (field of use). Usually saccharification process for bioethanol production does not require pure preparations, whereas application relating to aromas within food industry require higher purity in order to avoid desired taste of the end-product.

The composition may be in a liquid or as a solid form. The composition may be dried, spray-dried or lyophilized, granulated or otherwise concentrated and/or stabilized.

The present invention relates to a method of producing the polypeptide here described comprising:
  a. cultivating the recombinant host here described under conditions conducive for production of the polypeptide; and
  b. recovering the polypeptide.

Cultivating conditions are dependent on the host used. Optimization of the conditions and suitable fermentation medium can be done by a person skilled in the art.

The present invention relates to a method of hydrolysing biomass comprising contacting said biomass with the polypeptide here described or a composition here described.

In this connection term 'biomass' means especially cellulosic biomass including plant derived cellulosic and lignocellulosic (municipal or industrial) waste material, and e.g. cellulose-containing recycled material.

The present invention relates to a method for synthesis of di- and oligosaccharides and/or aryl-glycosides and/or alkyl-glycosides comprising contacting carbohydrate material with the polypeptide here described or a composition here described.

In this connection term 'carbohydrate material' means glucose, or a di- or oligosaccharide, or an aryl-glycoside or alkyl-glycoside containing material.

Beta-glucosidases can be used in synthesis of stereo- and regiospecific glycosides or oligosaccharides, which are in turn potentially useful as functional materials, nutraceuticals, or pharmaceuticals because of their biological recognition, signalling mechanisms, and antibiotic properties. Furthermore, beta-glucosidases can be used to synthetise disaccharides, such as sophorose or gentiobiose to act as inducers of cellulase synthesis in fungi. Some beta-glucosidases can also synthetise xylobiose or xylotriose that act as inducers for hemicellulase synthesis in fungi.

The present invention relates to also to a use of the polypeptides here described in hydrolysis or synthesis of glycosides.

It is to be understood that the terminology employed herein is for description and should not be regarded as limiting. It must be understood, that the embodiments given in the description above are for illustrative purposes only, and that various changes and modifications are possible within the scope of the disclosure.

The features of the invention described here as separate embodiments may also be provided in combination in a single embodiment. Also various features of the described here in the context of the method are usable in connection with the compositions and uses, and vice versa.

In the following the present invention will be described in more detail by means of examples. The purpose of the examples is not to restrict the scope of the claims but illustrate some embodiments.

EXAMPLES

Example 1. Cultivation of Fungal Strains for Transcriptome to Identify Genes Expressed Under the Selected Conditions Altogether 14 fungal strains from VTT culture collection were cultivated in shake flasks in two different culture media, the mycelia were collected, total RNA isolated and sequenced. GH1 beta-glucosidase genes which contained secretion signal were identified from the RNA sequencing data and the corresponding genes were expressed in the heterologous host *Trichoderma reesei*. The GH1 beta-glucosidase enzymes, that were produced and secreted in *T. reesei*, were analysed for their glucose tolerance and thermostability. The GH1 beta-glucosidases from *Penicilliopsis clavadiformis*, *Penicillium echinulatum* and *Talaromyces flavus* were showing the best properties and the corresponding original fungal strains were selected.

Cultivation Procedure

*Penicilliopsis clavadiformis* VTT-D-03941, *Penicillium echinulatum* VTT-D-92031 and *Talaromyces flavus* VTT-D-051105 fungal strains were cultivated in shake flasks in two different culture media. Medium 1 contained 10 g/l Solka floc cellulose, 10 g/l xylan (birch tree), 10 g/l gum (locust bean), 300 ml/l spent grain extract, 10 g/l yeast extract, 100 mM PIPPS, 8.6 g/l di-ammonium citrate, 5.4 g/l $(NH_4)_2SO_4$, 15.0 g/l $KH_2PO_4$, 2.4 mM $MgSO_4.7H_2O$, 4.1 mM $CaCl_2.H_2O$, 3.7 mg/l $CoCl_2$, 5 mg/l $FeSO_4.7H_2O$, 1.4 mg/l $ZnSO_4.7H_2O$, 1.6 mg/l $MnSO_4.7H_2O$. Medium 2 contained 10 g/l ground bagasse, 1 g/l citrus pectin, 10% olive oil, 10 g/l lactose, 10 g/l sorbitol, 10 g/l yeast extract, 100 mM PIPPS, 8.6 g/l di-ammonium citrate, 5.4 g/l $(NH_4)_2SO_4$, 15.0 g/l $KH_2PO_4$, 2.4 mM $MgSO_4.7H_2O$, 4.1 mM $CaCl_2.H_2O$, 3.7 mg/l $CoCl_2$, 5 mg/l $FeSO_4.7H_2O$, 1.4 mg/l $ZnSO_4.7H_2O$, 1.6 mg/l $MnSO_4.7H_2O$. pH of the medium was adjusted to 5.0 in both cases. The cultures were in each case inoculated with $8 \times 10^7$ spores/200 ml medium and grown in conical flasks at 28° C. with shaking at 250 rpm.

Collection of Mycelium Samples and Sample Treatment

Samples of mycelium were collected from the fungal cultivations at different time points by filtering through Whatman GF/B filters. After filtering, the samples were washed with equal volume of 0.7% NaCl, frozen immediately in liquid nitrogen, and stored at −80° C. Frozen mycelium was ground under liquid nitrogen using mortar and pestle, and total RNA from the samples was isolated using the Trizol™ Reagent (Gibco BRL) essentially according to manufacturer's instructions, and purified further by column purification, according to manufacturer's instructions (Qiagen).

RNA Sequencing

RNA isolated from cultures of *Penicillium echinulatum* after 5 days of cultivation, from cultures of *Penicifﬁopsis clavariiformis* after 3 and 5 days of cultivation, and from cultures of *Talaromyces flavus* after 3 and 5 days of cultivation, was subjected to de novo RNA sequencing. Library preparation (TruSeq stranded mRNA) for the sequencing, and the sequencing (by Illumina NextSeq 500 sequencing, generating 150 bp paired-end reads, about 25 million reads per sample) were carried out by SourceBioscience company. The sequence data was adapter- and quality-trimmed using Skewer software (version 0.1). De novo assembly of the RNA sequencing reads into a transcriptome was done using Trinity software.

Example 2. Identification of Putative Secreted GH1 Family Beta-Glucosidase Genes from the RNA Sequencing Data GH1 family beta-glucosidases were searched from the amino acid sequences generated from the transcriptome databases described in Example 1 using Basic Local Alignment Search Tool (tBLASTn, Altschul et al. 1990) and using following query protein sequences (Uniprot accession codes): O93785 (v1), Q9C122 (v1), Q25BW5 (v1), Q9P456 (v1), O93784 (v1), Q9UUQ3 (v1), Q7Z9M2 (v1) and O93785 (v1). The Blast hit sequences were analysed for secretion signal peptide using SignalP software (Nordahl Petersen et al. 2011.

Surprisingly, secretion signal peptide was found in three sequences derived from *Penicifﬁopsis clavariiformis* (translated coding sequence of SEQ ID NO: 2), *Talaromyces flavus* (translated coding sequence of SEQ ID NO: 4), *Penicillium echinulatum* (translated coding sequence of SEQ ID NO: 6) These sequences were further analysed with InterProScan, which confirmed the presence signal peptide and GH1 catalytic domain. In addition, it was found out that the sequences contained ca 150 amino acid long N-terminal extension, which was not found in the intracellular GH1 enzymes (e.g. in the Blast query sequences).

Example 3. Creation of *Trichoderma reesei* Strains to Express the Beta-Glucosidases To construct the expression vectors, genes encoding secreted GH1 beta-glucosidases from *Talaromyces flavus* (TalaromycesFlav_c22328_g1), *Penicilliopsis clavariiformis* (PenicilliopsisClav_v2_c11509_g1), *Penicillium echinulatum* (PenicilliumEchi_v2_c28458_g1) were codon optimized for *T. reesei* expression and synthesized by the GeneArt company. The sequence for the native secretion signal was left out from the beta-glucosidases sequences and signal sequence of CBHI (MYRKLAVISAFLATARA; SEQ ID NO: 7) was added to N-terminus of the beta-glucosidases to ensure efficient secretion. The expression vectors were assembled with the yeast (*Saccharomyces cerevisiae*) recombination cloning method. The fragments for cloning were cut from the GeneArt plasmids with restriction enzymes and were inserted into PacI linearized pTTv248 vector backbone. FIG. 1 shows the design of the *T. reesei* expression cassette for expression of the GH1 beta-glucosidases (GOI=gene of interest and hphR=selection for hygromycine resistance). The expression vector contained targeting sequence for the cbh1 locus, cbh1 promoter and terminator and the hphR selection marker. After plasmid rescue and transformation into E. coli, all constructs were verified by DNA sequencing. The expression cassettes were liberated from the expression plasmids (B7852, B7850, B7854 for T. flavus, P. clavariiformis and P. echinulatum beta-glucosidases, respectively) with PmeI restriction enzyme prior to transformation.

To generate the beta-glucosidase producing strains, the T. reesei M362 strain that is deleted for three major cellulases (cbh2, egl1, egl2) was transformed with the expression cassettes and grown on MM+hygromycin transformation plates. Transformants were screened first by PCR for 5' and 3' flank integration into the cbh1 locus and absence of the open reading frame for cbh1. The final beta-glucosidase producing T. reesei strains devoid of four major cellulase genes (cbh1, cbh2, egl1, egl2) were named as M2003 and M2004 for two parallel strains producing T. flavus beta-glucosidase, as M1999 and M2000 for parallel strains producing P. clavariiformis beta-glucosidase, and as M2007 and M2008 for strains producing P. echinulatum beta-glucosidase.

Beta-Glucosidase Production Strains Grown in 24-Well Microtiter Plates

Figure 2:
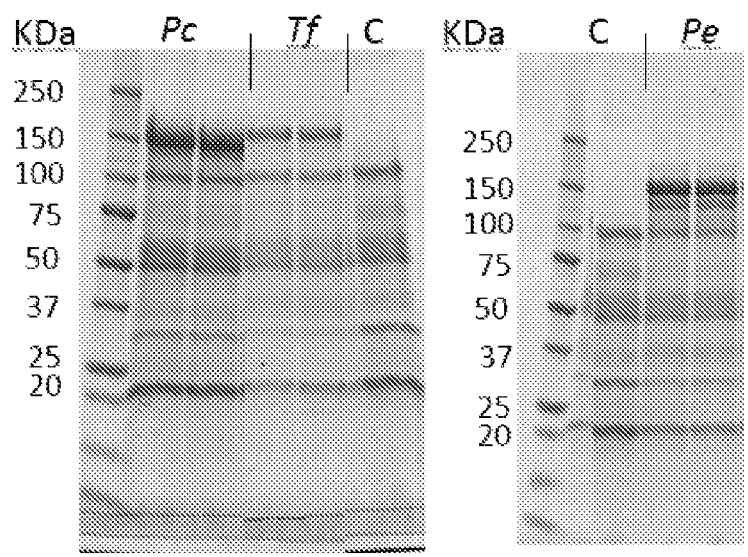
FIG. 2 shows culture supernatants (a 10 ul) analysed on SDS-PAGE after 5 days of cultivation of the *T. reesei* strains producing *P. clavariiformis* beta-glucosidase (Pc), *T. flavus* beta-glucosidase (Tf) and *P. echinulatum* beta-glucosidase (Pe). As the Control (C) culture supernatant from *T. reesei* strain M362 was used.

The T. reesei production strain transformants were grown in 24-well microtiter plates in TrMM medium, which contained additionally 40 g/L lactose, 20 g/L spent grain extract, 8.6 g/L diammonium citrate, 5.4 g/L NaSO$_4$, 100 mM PIPPS at pH 4.5, shaking at 28° C. at 800 rpm (Infors AG). TrMM medium contains 7.6 g/L (NH$_4$)$_2$SO$_4$, 15.0 g/L KH$_2$PO$_4$, 2.4 mM MgSO$_4$-7H$_2$O, 4.1 mM CaCl$_2$)—H$_2$O, 3.7 mg/L CoCl$_2$, 5 mg/L FeSO$_4$-7H$_2$O, 1.4 mg/L ZnSO$_4$-7H$_2$O and 1.6 mg/L MnSO$_4$-7H$_2$O (Penttila et al., 1987). SDS-PAGE gel analysis was done to detect beta-glucosidase proteins produced into the culture supernatant after 5 days cultivation. 10 μl of the culture supernatant was loaded into the 4-20% Criterion gel (BioRad). Sample was mixed with Laemmli sample buffer containing 3-mercaptoethanol and heated at 95° C. for 5 minutes. These samples loaded into a 4-20% SDS PAGE gel (BioRad TGX Criteron precast gel) along with Precision Plus Protein Standard as molecular weight marker (BioRad). The gel was run in SDS-PAGE running buffer for 30 minutes at 200 V. The gel was stained with GelCode blue stain and destained with water for 2 hours. The gels were scanned with the Licor Biosciences CLx at 700 nm. The results are shown in FIG. 2: Culture supernatants (a 10 ul) analysed on SDS-PAGE after 5 days of cultivation of the T. reesei strains producing P. clavariiformis beta-glucosidase (Pc), T. flavus beta-glucosidase (Tf) and P. echinulatum beta-glucosidase (Pe). As the Control (C) culture supernatant from T. reesei strain M362 was used.

Example 4. Glucose Tolerance of the Novel GH1 Beta-Glucosidases

The beta-glucosidase activity in the T. reesei culture supernatant samples was measured with 1 mM p-nitrophenyl beta-D-glucopyranoside (pNPG) as substrate in 50 mM Na-citrate buffer pH 5 at 50° C. (reaction volume 0.15 ml, containing 0.015 ml enzyme sample), in the presence of 0-800 mM glucose. The reaction was terminated after 10 minutes by addition of 0.075 ml 1 M Na$_2$CO$_3$. The released p-nitrophenol was quantified with spectrophotometer at 400 nm against standard curve prepared from 0.05-0.5 μmol/ml p-nitrophenol. The control reactions were incubated without the enzyme samples, and only after addition of the 1 M Na$_2$CO$_3$, 0.015 ml of buffer or enzyme was added. A commercial beta-glucosidase enzyme preparation, Novozym 188 (NZ188), was used as reference. The activity values in the FIG. 3 are presented as % residual activity compared to the measurement carried out in absence of glucose.

Example 5. Thermal Stability of Beta-Glucosidases

The protein concentrations in the samples were measured with BioRad DC kit (BioRad, Berkley, Calif.) according to the manufacturer's instruction using bovine serum albumin (BSA) as a standard. The proteins in the samples were precipitated with acetone (0.2 ml samples+0.6 ml acetone, incubation at −20° C. overnight) and resolubilised in 50 mM Na-acetate buffer pH 5. The enzyme samples (at concentration 0.1 mg protein/ml) were incubated at 4° C., 45° C. or 60° C. for 21 h in 50 mM Na-citrate buffer pH 5 containing 0.1 mg BSA/ml.

After the incubation, the beta-glucosidase activity in the samples was measured with 1 mM p-nitrophenyl beta-D glucopyranoside (pNPG) as substrate in 50 mM Na-citrate buffer pH 5 at 50° (reaction volume 0.15 ml, containing 0.015 ml enzyme sample, 10 min assay). The reaction was terminated by addition of 0.075 ml 1 M Na$_2$CO$_3$. The released p-nitrophenol was quantified with spectrophotometer at 400 nm against standard curve prepared from 0.05-0.5 μmol/ml p-nitrophenol. The control reactions were incubated without the enzyme samples, and only after addition of the 1 M Na$_2$CO$_3$, 0.015 ml of buffer or enzyme were added. A commercial beta-glucosidase enzyme preparation, Novozym 188 (NZ188), was used as reference. The thermostabilities in FIG. 4 are presented as % residual activity.

Figure 6:
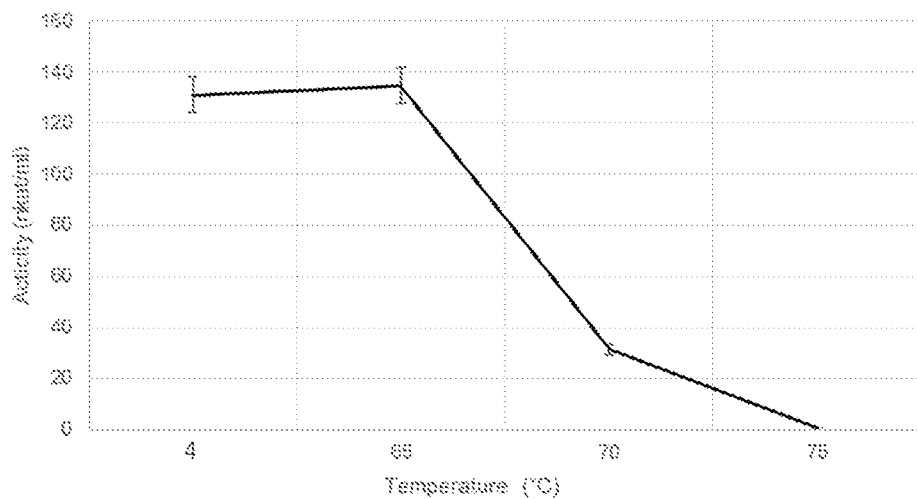
FIG. 6 shows the thermostability of the non-purified Pc_GH1 beta-glucosidase preparation at elevated temperatures. The enzyme samples were incubated at pH 5, at 4, 65, 70 and 75° C. for 2 h, after which the activity (nkat/ml) was measured at pH 5, 50° C. using pNPG as a substrate.

Thermostability of the non-purified Pc_GH1 sample was further investigated by incubating the T. reesei culture supernatant sample at different temperatures (65, 70, 75° C.) for 2 h. The culture supernatant samples were exchanged into 50 mM Na-acetate buffer, pH 5, prior incubation. After incubation, the residual activities of the samples were measured at pH 5, 50° C. and are shown in FIG. 6.

Example 6. Purification of Beta-Glucosidases

The protease inhibitors as a CO-RO Roche cOmplete Protease Inhibitor Cocktail (Sigma-Aldrich) were added to the crude Pc_GH1 enzyme preparation (i.e. culture supernatant) produced in T. reesei (1 Tablet/50 ml solution). The sample was then heat treated at +60° C. water bath (Jeio Tech, Korea) for 20 h, after which the precipitated proteins were removed by centrifugation (5 min, 2000×g, Eppendorf 5819R, swing-out). The supernatant, containing the Pc_GH1 enzyme, was collected to a syringe and filtered through 0.45 um pore size syringe filter (Ø 30 mm, Whatman, GE-healthcare). The clarified sample was concentrated in VivaSpin tubes (cut off 10000 Da) and changed into 10 mM phosphate buffer (pH 6.1) using prepacked Sephadex G-25 Coarse column. The sample was then applied into a 20 ml anion exchange column HiPrep 16/10 DEAE FF. The buffer system used was composed of buffers A) 10 mM sodium phosphate buffer (pH 6.1) and B) 10 mM sodium phosphate buffer (pH 6.1) containing 1 M sodium chloride. After sample application, the anion exchange column was first washed with 10% buffer B (55 CV) and the Pc_GH1 was eluted with linear gradient of 10-25% of the buffer B (33 CV).

The reference GH3 family beta-glucosidase An Cel3A from Aspergillus niger was purified from the commercial enzyme preparation Novozym 188 (NZ188, Novozymes) according to Sipos et al. (2010). The reference GH1 family beta-glucosidase Nt_GH1 from termite *Nasutitermes takasagoensis* (GeneBank accession code BAI50022.1) was produced in *E. coli* and purified from cell lysate with an immobilised metal affinity chromatography (IMAC) column using His$_6$-tag included in the recombinant enzyme sequence.

Example 7. pH Optima and Stability of Beta-Glucosidases

Figure 7:
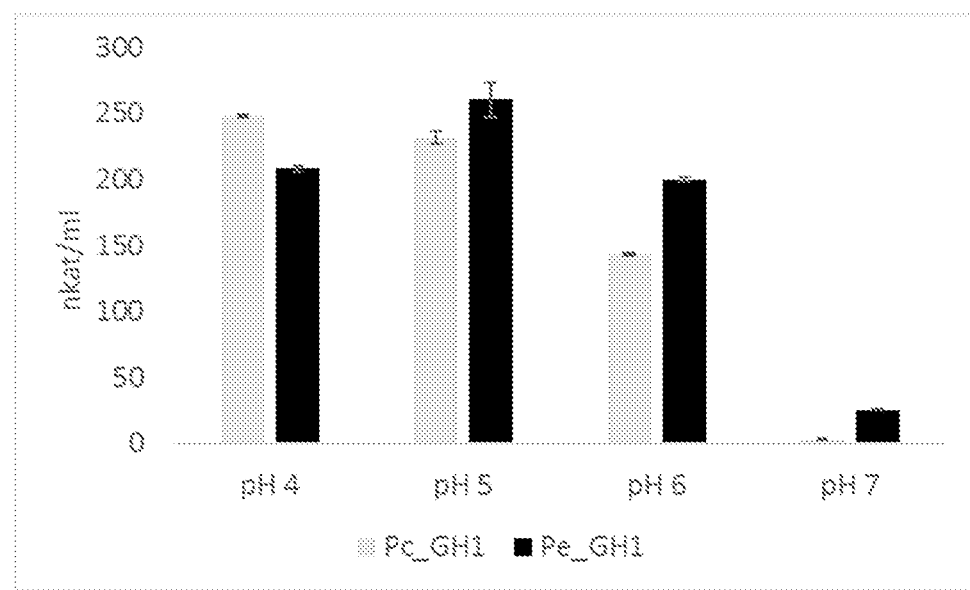
FIG. 7 shows the pH activity profiles of the non-purified Pc_GH1 and Pe_GH1 beta-glucosidase preparations. The activity (nkat/ml) was measured using pNPG as a substrate at pH range 4-7, at 50° C.

The effect of pH on the beta-glucosidase activity of the crude Pc_GH1 and Pe_GH1 preparations produced in *T. reesei* were measured using 1 mM p-nitrophenyl beta-D-glucopyranoside (pNPG) as substrate in 50 mM Na-citrate pH 4, 5 and 6 and 50 mM Tris-HCl 7, at 50° C. (reaction volume 0.5 ml, containing 0.05 ml enzyme dilution). The reaction was terminated after 10 minutes by addition of 0.25 ml 1 M Na$_2$CO$_3$. The released p-nitrophenol was quantified with spectrophotometer at 400 nm against standard curve prepared from 0.05-0.5 μmol/ml p-nitrophenol. Standards were prepared for each pH separately. The control reactions were incubated without the enzyme samples, and only after addition of the 1 M Na$_2$CO$_3$, 0.05 ml of buffer or enzyme was added. The columns in FIG. 7 show the activity (nkat/ml) of the culture supernatant samples in each measured pH.

Figure 8:
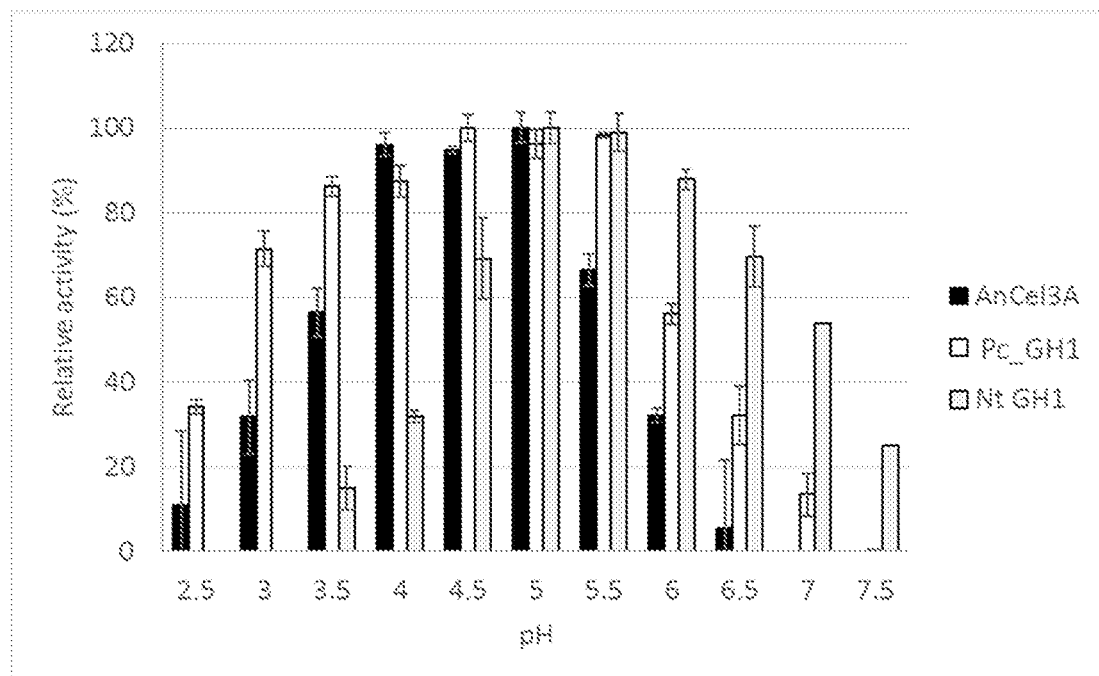
FIG. 8 shows the relative activity profiles of the purified beta-glucosidase Pc_GH1 and two reference beta-glucosidases An Cel3A and Nt_GH1 measured at pH range 2.5-7.5, at 50° C. The highest activity value has been in each three cases taken as the 100% value.
Figure 9:
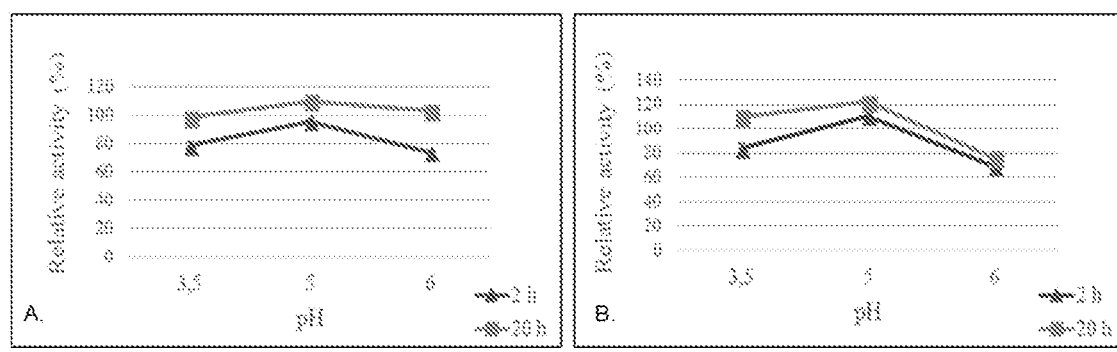
FIG. 9 shows the pH stability of the purified Pc_GH1 (A) and the reference An Cel3A enzyme (B) at pH 3.5, 5.0 and 6.0 after incubation at elevated temperature of 50° C. for 2 h and 20 h. The pH activity curves represent the relative activities as compared to enzyme preparation stored at 4° C. (in each corresponding pH, and for both incubation time), which has been taken as the 100% value.
Figure 10:
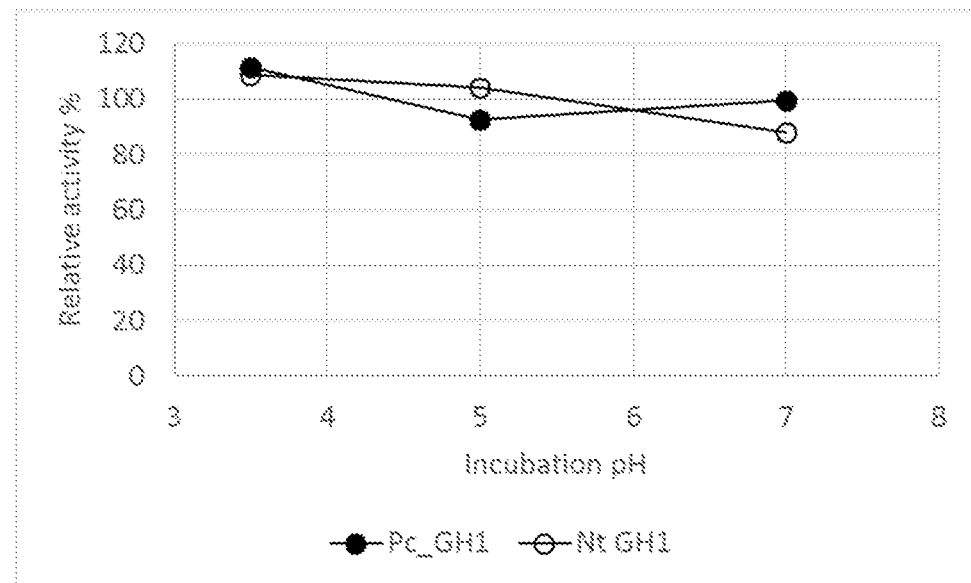
FIG. 10 shows the pH stability of the purified Pc_GH1 and the reference Nt_GH1 beta-glucosidase at pH 3.5, 5.0 and 7.0 after incubation at 30° C. for 2 h. The pH activity curves represent the relative activities as comparison to enzyme preparation stored at 4° C. (in each corresponding pH), which has been taken as the 100% value.

To determine the pH optima for purified beta-glucosidases, the enzyme activity was assayed using 2 mM pNPG as substrate in 75 mM McIlvaine buffer pH 2.5-7.5 at 50° C. (reaction volume 0.15 ml, including 0.015 ml enzyme dilution). The reaction was terminated after 10 minutes by addition of 0.075 1 M Na$_2$CO$_3$. The activity was quantified as above. The activity values of purified Pc_GH1 and the reference enzymes An Cel3A and Nt_GH1 are shown in FIG. 8 as % of the maximal activity of each enzyme.

pH stability of purified beta-glucosidases Pc_GH1 as a comparison to the known GH3 family beta-glucosidase AnCel3A was compared using 75 mM McIlvaine buffer system at pH values of 3.5, 5.0 and 6.0, at 50° C. The protein samples (approximately 20 μg/ml) were incubated in each pH for 2 h and 20 h. After that, the samples were diluted (600-1000-fold) to 50 mM sodium acetate (pH 5) prior to the activity measurements (using 1 mM pNPG in 50 mM Na-citrate pH 5). Half of the purified protein samples in each pH were kept at refrigerator (+4° C.) for the duration of incubation (2 h or 20 h). The relative activities (%) measured at 50° C. vs. 4° C. at each pH value are shown in FIG. 9.

pH stability of the purified Pc_GH1 as a comparison to the known GH1 family beta-glucosidase Nt_GH1 was compared at pH values of 3.5, 5.0 and 7.0 in a similar manner as described above, at temperatures of 4 and 30° C. after 2 h incubation. Protein concentrations in the experiment were 15 μg/ml. The activities are shown in FIG. 10.

Example 8. Substrate Specificity of Beta-Glucosidases

Figure 11:
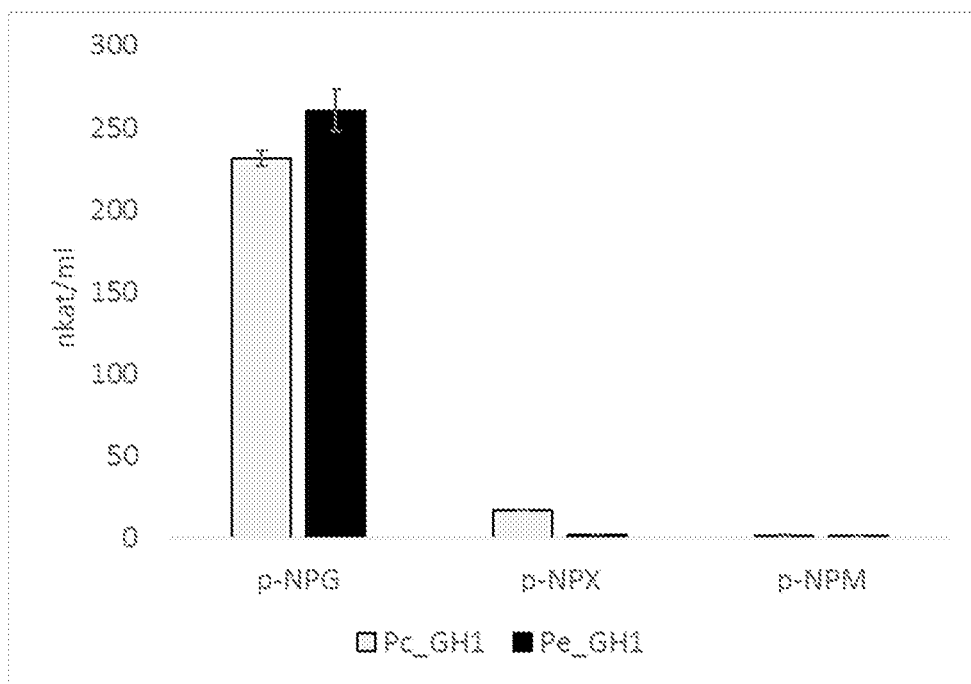
FIG. 11 shows the substrate specificity of the non-purified Pc_GH1 and Pe_GH1 enzyme preparations measured with three different chromophoric substrates (a 1 mM), p-nitrophenyl-β-D glucopyranoside (pNPG), p-nitrophenyl-β-D mannopyranoside (pNPM) and p-nitrophenyl-β-D xylopyranoside (pNPX), at pH 5, 50° C. in a 10-minute reaction.

The activity of the non-purified Pc_GH1 and Pe_GH1 enzyme preparations towards 1 mM p-nitrophenyl beta-D-glucopyranoside (p-NPG), p-nitrophenyl beta-D-xylopyranoside (p-NPX) and p-nitrophenyl beta-D-mannopyranoside (p-NPM) was measured in 50 mM Na-citrate buffer 5 at 50° C. (reaction volume 0.5 ml, containing 0.05 ml enzyme dilution). The reaction was terminated after 10 minutes by addition of 0.25 ml 1 M Na$_2$CO$_3$. The released p-nitrophenol was quantified with spectrophotometer at 400 nm against standard curve prepared from 0.05-0.5 μmol/ml p-nitrophenol. The columns in the FIG. 11 show the measured activity (nkat/ml) of the culture supernatant sample with each three substrates.

The activity of purified Pc_GH1 and the reference beta-glucosidases An Cel3A and Nt_GH1 were measured with 2 mM p-nitrophenyl-β-D glucopyranoside (p-NPG), p-nitrophenyl-β-D galactopyranoside (p-NPGal), p-nitrophenyl-β-D mannopyranoside (pNPM), p-nitrophenyl-β-D xylopyranoside (pNPX), p-nitrophenyl-β-D fucopyranoside (pNPF) at 50° C., pH 5 (reaction volume 0.15 ml, including 0.015 ml enzyme dilution). The reaction was terminated after 10 min by addition of 0.075 1 M Na$_2$CO$_3$. The activity was quantified as above. Concerning p-nitrophenyl-β-D mannopyranoside (pNPM), p-nitrophenyl-β-D xylopyranoside (pNPX), and p-nitrophenyl-β-D fucopyranoside (pNPF), also activity after 2 h reaction time was measured in a similar manner as described above (using 2 mM substrate concentration). The specific activities after 10 min reaction time are shown in Table 1 and those after 2 h reaction time in Table 2.

TABLE 1

Specific activity of purified Pc_GH1 and reference enzymes An Cel3A and Nt GH1 towards 2 mM p-nitrophenyl-β-D glucopyranoside (p-NPG), p-nitrophenyl-β-D galactopyranoside (p-NPGal), p-nitrophenyl-β-D mannopyranoside (pNPM), p-nitrophenyl-β-D xylopyranoside (pNPX), p-nitrophenyl-β-D fucopyranoside (pNPF) measured at pH 5, 50° C. after 10 min reaction time.

| | Specific activity (nkat/mg prot) | | |
| --- | --- | --- | --- |
| Substrate | AnCel3A | Pc_GH1 | Nt GH1 |
| pNPG | 2320 | 2400 | 240 |
| pNPGal | — | 18.6 | 42.4 |
| pNPM | — | — | 4.2 |
| pNPX | — | 16.9 | — |
| pNPF | — | 500 | 957 |

TABLE 2

Activities of purified Pc_GH1 and reference enzymes An Cel3A and Nt GH1 towards 2 mM p-nitrophenyl-β-D galactopyranoside (p-NPGal), p-nitrophenyl-β-D mannopyranoside (pNPM) and p-nitrophenyl-β-D xylopyranoside (pNPX) measured at pH 5, 50° C. after 2 h reaction time.

| | Specific activity (nmol/min/mg prot) | | |
| --- | --- | --- | --- |
| Substrate | AnCel3A | Pc_GH1 | Nt GH1 |
| pNPGal | 64 | 407 | 294 |
| pNPM | 48 | — | 13 |
| pNPX | 122 | 386 | 42 |

Example 9. Effect of Ethanol on the Pc_GH1 Activity

Figure 12:
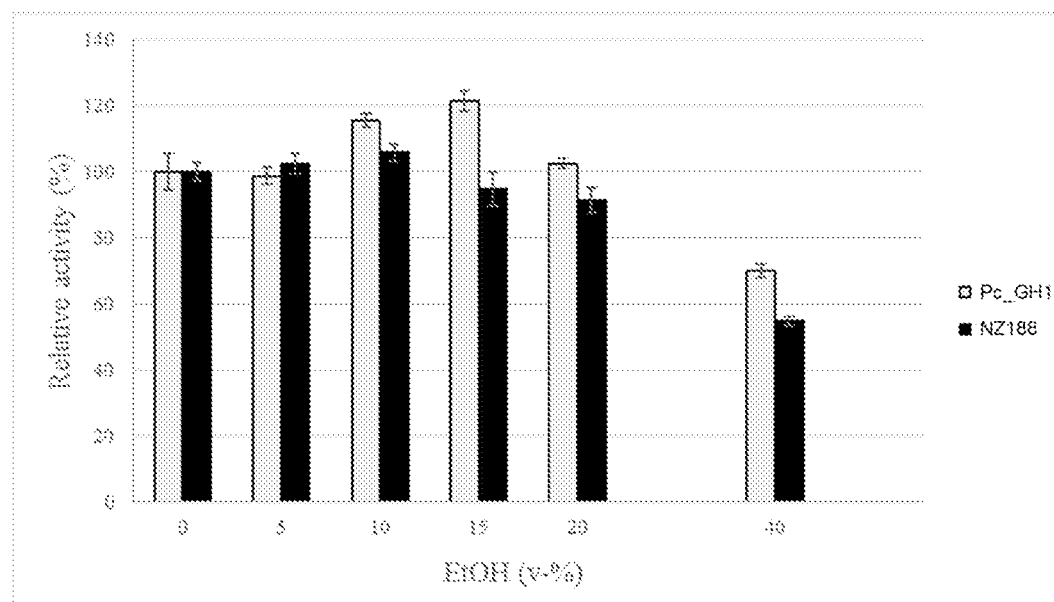
FIG. 12 shows the effect of ethanol (5, 10, 15, 20 and 40%) on the beta-glucosidase activity of the partially purified Pc_GH1 and the reference enzyme Novozym 188 (NZ188) measured at pH 5, 30° C. The activity without added ethanol ("0%") was in both cases taken as 100%.

Effect of ethanol on the beta-glucosidase activity of Pc_GH1 and the commercial reference Novozym 188 (NZ188) was compared by measuring the beta-glucosidase activity using 2 mM pNPG as substrate in presence of 5, 10, 15, 20 and 40% ethanol (v/v). The assay was carried out in 50 mM Na citrate buffer pH 5, at 30° C. (the latter in order to minimize ethanol evaporation) in a reaction volume 1.125 ml. The quantification of enzyme activity was carried out as in Example 7. The activities in FIG. 12 are in both cases presented as relative activities (%) as compared to the activity in the absence of ethanol.

Figure 13:
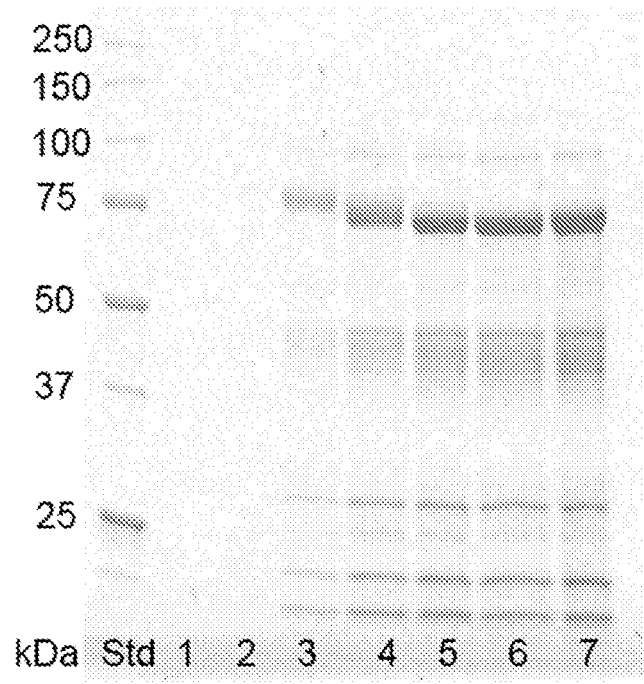
FIG. 13 shows the SDS-PAGE analysis of the supernatant samples taken from the 144 h and 53 min fermentor cultivation of *Trichoderma reesei* strain producing Pc_GH1 beta-glucosidase. The lanes 1-7 are samples taken from time-points (h:min) 1): 0:15 2) 20:23 3) 44:18, 4) 68:20, 5) 92:20, 6) 121:08 and 7) 144:53).

Example 10. Cultivating the *T. reesei* Strain Expressing the Pc_GH1 in a Fermentor Scale The *T. reesei* strain expressing the gene encoding Pc_GH1 was cultivated in 20 l fermentor The soluble protein concentration in the fermentor samples was quantified after precipitation with equal volume of 10% trichloroacetic acid for 0.5 h at 4° C. The protein pellet was redissolved in Lowry buffer A (20 g $Na_2CO_3$, 4 g NaOH) and the soluble protein concentration was measured with BioRad DC kit according to manufacturer's instruction and using bovine serum albumin as standard. After 144:53 h cultivation, the total protein concentration was 14 g/l. The soluble protein composition in fermentation samples, taken at different time points (timepoints (h:min) 0:15, 20:23, 44:18, 68:20, 92:20, 121:08 and 144:53) was analysed with SDS-PAGE using 4-20% BioRad Criterion Stain Free gradient Gels and BioRad Stain Free Imaging system. The Pc_GH1 protein was found to the major component in all the fermentor samples (FIG. 13).

REFERENCES

Penttilä M, Nevalainen H, Ratto M, Salminen E, Knowles J. A versatile transformation system for the cellulolytic filamentous fungus *Trichoderma reesei*. Gene 1987; 61(2): 155-164. pmid:3127274

Altschul, S. F., Gish, W., Miller, W., Myers, E. W. & Lipman, D. J. (1990) "Basic local alignment search tool." J. Mol. Biol. 215:403-410.

Nordahl Petersen T, Brunak S, von Heijne G & Nielsen H (2011) SignalP 4.0: discriminating signal peptides from transmembrane regions. Nat Methods, 8: 785-786

Sipos, B., Benkő, Z., Dienes, D., Réczey, K., Viikari, L., Siika-Aho, M. (2010). 'Characterisation of specific activities and hydrolytic properties of cell-wall-degrading enzymes produced by *Trichoderma reesei* Rut C30 on different carbon sources'. Applied biochemistry and biotechnology, 161(1-8), pp. 347-364

The invention claimed is:

1. A recombinant polypeptide having beta-glucosidase activity, the recombinant polypeptide comprising:
   a. a polypeptide having at least 90% identity to the sequence of mature polypeptide of SEQ ID NO: 1; or
   b. a polypeptide encoded by the nucleotide that hybridizes under high stringent conditions of an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. with the complement of the sequence encoding the mature polypeptide defined by SEQ ID NO: 1,
   wherein, a fragment of the polypeptide of (a) or (b) comprises amino acid residues in positions 145 to 602 of SEQ ID NO: 1.

2. The polypeptide of claim 1, wherein the polypeptide maintains at least 40% of its relative catalytic activity at pH 3 to 5.5.

3. The polypeptide of claim 1, wherein the polypeptide maintains full activity at 200 mM glucose concentration.

4. An isolated polynucleotide encoding the polypeptide of claim 1, wherein the codon usage has been optimized for a desired production host.

5. A method of hydrolysing biomass comprising contacting said biomass with the polypeptide of claim 1.

6. A method for synthesis of oligosaccharides or aryl-glycosides or alkyl-glycosides, the method comprising contacting carbohydrate material with the polypeptide of claim 1.

7. A recombinant polypeptide produced by an isolated recombinant host cell comprising a polynucleotide operably linked to one or more control sequences directing the production of the recombinant polypeptide in the recombinant host, wherein the recombinant polypeptide has beta-glucosidase activity and comprises:

a. a polypeptide having at least 90% identity to the sequence of mature polypeptide of SEQ ID NO: 1; or
 b. a polypeptide encoded by the nucleotide that hybridizes under high stringent conditions of an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. with the complement of the sequence encoding the mature polypeptide defined by SEQ ID NO: 1,
 wherein, a fragment of the polypeptide of (a) or (b) comprises amino acid residues in positions 145 to 602 of SEQ ID NO: 1.

8. A recombinant polypeptide having beta-glucosidase activity, wherein the recombinant polypeptide has at least 90% identity to the sequence of mature polypeptide of SEQ ID NO: 1 and comprises amino acid residues in positions 145 to 602 of SEQ ID NO: 1.

* * * * *